US007638570B2

(12) United States Patent
Torii et al.

(10) Patent No.: US 7,638,570 B2
(45) Date of Patent: Dec. 29, 2009

(54) WATER-ABSORBING AGENT

(75) Inventors: Kazushi Torii, Himeji (JP); Yoshiro Mitsukami, Himeji (JP); Motohiro Imura, Akashi (JP); Taku Iwamura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 380 days.

(21) Appl. No.: 10/544,337

(22) PCT Filed: Feb. 2, 2004

(86) PCT No.: PCT/JP2004/001007

§ 371 (c)(1),
(2), (4) Date: Aug. 3, 2005

(87) PCT Pub. No.: WO2004/069915

PCT Pub. Date: Aug. 19, 2004

(65) Prior Publication Data
US 2006/0204755 A1 Sep. 14, 2006

(30) Foreign Application Priority Data
Feb. 10, 2003 (JP) .............................. 2003-032698

(51) Int. Cl.
C08L 31/02 (2006.01)
A61L 15/60 (2006.01)
(52) U.S. Cl. .................. 524/430; 524/436; 524/437; 524/444; 524/445; 524/447; 524/451; 524/543; 524/556; 524/560; 502/400; 502/401; 502/402; 604/358
(58) Field of Classification Search ............... 524/430, 524/436, 437, 444, 445, 447, 451, 543, 556, 524/560; 502/400, 401, 402; 604/358
See application file for complete search history.

(56) References Cited

U.S. PATENT DOCUMENTS

| 4,093,776 | A | 6/1978 | Aoki et al. |
|---|---|---|---|
| 4,367,323 | A | 1/1983 | Kitamura et al. |
| 4,446,261 | A | 5/1984 | Yamasaki et al. |
| 4,625,001 | A | 11/1986 | Tsubakimoto et al. |
| 4,683,274 | A | 7/1987 | Nakamura et al. |
| 4,690,996 | A | 9/1987 | Shih et al. |
| 4,721,647 | A | 1/1988 | Nakanishi et al. |
| 4,734,478 | A | 3/1988 | Tsubakimoto et al. |
| 4,738,867 | A | 4/1988 | Itoh et al. |
| 4,748,076 | A | 5/1988 | Saotome |
| 4,769,427 | A | 9/1988 | Nowakowsky et al. |
| 4,876,299 | A | 10/1989 | Avar |
| 4,950,692 | A | 8/1990 | Lewis et al. |
| 5,051,259 | A | 9/1991 | Olsen et al. |
| 5,164,459 | A | 11/1992 | Kimura et al. |
| 5,264,495 | A | 11/1993 | Irie et al. |
| 5,419,956 | A | 5/1995 | Roe |
| 5,478,879 | A | 12/1995 | Kajikawa et al. |
| 5,760,080 | A | 6/1998 | Wada et al. |
| 5,797,893 | A | 8/1998 | Wada et al. |
| 5,849,405 | A | 12/1998 | Wang et al. |
| 5,851,672 | A | 12/1998 | Wang et al. |
| 6,054,541 | A | 4/2000 | Wada et al. |
| 6,087,450 | A | 7/2000 | Breitbach et al. |
| 6,099,950 | A | 8/2000 | Wang et al. |
| 6,180,724 | B1 | 1/2001 | Wada et al. |
| 6,228,930 | B1 | 5/2001 | Dairoku et al. |
| 6,391,451 | B1 | 5/2002 | Mitchell et al. |
| 6,414,214 | B1 | 7/2002 | Engelhardt et al. |
| 6,433,058 | B1 | 8/2002 | Weir et al. |
| 6,605,673 | B1 | 8/2003 | Mertens et al. |
| 6,620,889 | B1 | 9/2003 | Mertens et al. |
| RE38,444 | E | 2/2004 | Wada et al. |
| 2002/0128618 | A1 | 9/2002 | Frenz et al. |
| 2002/0169252 | A1 | 11/2002 | Wilson |
| 2002/0193492 | A1 | 12/2002 | Wilson |
| 2003/0020199 | A1 | 1/2003 | Kajikawa et al. |
| 2003/0060112 | A1 | 3/2003 | Rezai et al. |
| 2003/0207997 | A1 | 11/2003 | Mertens et al. |
| 2007/0129495 | A1 | 6/2007 | Mertens et al. |

FOREIGN PATENT DOCUMENTS

DE 198 13 443 10/1998

(Continued)

OTHER PUBLICATIONS

Modern Superabsorbent Polymer Technology, Wiley-VCH, ISBN 0-471-19411-5, pp. 72-74, 93-103, 130 and 131, 1997.

(Continued)

Primary Examiner—Ana L Woodward
(74) Attorney, Agent, or Firm—Roylance, Abrams, Berdo & Goodman, L.L.P.

(57) ABSTRACT

There is disclosed a water-absorbing agent which combines both performances of the capillary suction force and the liquid permeability. This water-absorbing agent is a particulate water-absorbing agent comprising water-absorbent resin particles (α) and a liquid-permeability-enhancing agent (β), wherein the water-absorbent resin particles (α) are surface-crosslink-treated particles of a crosslinked polymer of a monomer including acrylic acid and/or its salt; with the water-absorbing agent being characterized in that the particulate water-absorbing agent has: a mass-average particle diameter (D50) in the range of 234 to 394 gm, a logarithmic standard deviation (σζ) of a particle diameter distribution in the range of 0.25 to 0.45, an absorption capacity without load (CRC) of not less than 15 g/g, and a water-extractable component content of not higher than 15 mass %; and further a liquid-permeability-enhancing agent (β) content in the range of 0.01 to 5 mass parts per 100 mass parts of the water-absorbent resin particles (α).

12 Claims, 7 Drawing Sheets

FOREIGN PATENT DOCUMENTS

| | | |
|---|---|---|
| EP | 0 349 240 | 1/1990 |
| EP | 0 640 330 | 3/1993 |
| EP | 0 629 411 | 12/1994 |
| EP | 0 668 080 | 8/1995 |
| EP | 0 761 241 | 3/1997 |
| EP | 0 844 270 | 5/1998 |
| EP | 0 579 764 | 8/1999 |
| EP | 0 951 913 | 10/1999 |
| EP | 1 029 886 | 8/2000 |
| EP | 1 178 059 | 2/2002 |
| JP | 6-25209 | 4/1994 |
| JP | 07-116511 | 5/1995 |
| JP | 08-057310 | 3/1996 |
| JP | 9-509591 | 9/1997 |
| JP | 9-290000 | 11/1997 |
| JP | 11-58615 | 3/1999 |
| JP | 11-240959 | 9/1999 |
| JP | 2000-109714 | 4/2000 |
| JP | 2001-89527 | 4/2001 |
| JP | 2002-121291 | 4/2002 |
| WO | WO 95/22356 | 8/1995 |
| WO | WO 95/26209 | 10/1995 |
| WO | WO 96/01608 | 1/1996 |
| WO | WO 97/12575 | 4/1997 |
| WO | WO 97/25013 | 7/1997 |
| WO | WO 97/34558 | 9/1997 |
| WO | WO 98/06364 | 2/1998 |
| WO | WO 98/47454 | 10/1998 |
| WO | WO 98/48857 | 11/1998 |
| WO | WO 00/53644 | 9/2000 |
| WO | WO 00/53664 | 9/2000 |
| WO | WO 01/66056 | 9/2001 |
| WO | WO 01/89591 A2 * | 11/2001 |

OTHER PUBLICATIONS

Ullmann's Encyclopedia of Industrial Chemistry, 6th Ed., vol. 35, Wiley-VCH, ISBN 3-527-30385-5, pp. 73, 80, 81, 84 and 85, 2003.

* cited by examiner

Fig. 5  Logarithmic normal probability paper

WATER-ABSORBING AGENT

TECHNICAL FIELD

The present invention relates to a water-absorbing agent. More specifically, the present invention relates to a water-absorbing agent which combines excellent capillary suction force and liquid permeability wherein the water-absorbing agent is obtained by: modifying surfaces of, water-absorbent resin particles ($\alpha$) with a crosslinking agent, wherein the water-absorbent resin particles ($\alpha$) are regulated to a specific mass-average particle diameter and a specific particle diameter distribution; and containing a liquid-permeability-enhancing agent ($\beta$).

BACKGROUND ART

At present, water-absorbent resins (water-absorbing agents) and hydrophilic fibers (e.g. pulp) are widely used for sanitary materials such as disposable diapers, sanitary napkins, and so-called incontinent pads as their component materials for the purpose of causing the water-absorbent resins and the hydrophilic fibers to absorb body fluids. Examples of materials used as main raw materials for the above water-absorbent resins include: partially-neutralized and crosslinked poly(acrylic acids); hydrolyzed graft polymers of starch-acrylic acid; saponified copolymers of vinyl acetate-acrylic acid ester; hydrolyzed copolymers of acrylonitrile or acrylamide, or crosslinked polymers of these hydrolyzed copolymers; and crosslinked polymers of cationic monomers.

In recent years, as to these sanitary materials such as disposable diapers and sanitary napkins, their high functionalization and thinning are making progress, so there is a tendency toward increases in the amount of the water-absorbent resin as used per piece of sanitary material and in mass % of the water-absorbent resin relative to a whole absorbent structure consisting of such as the water-absorbent resin and the hydrophilic fibers. Specifically, the ratio of the water-absorbent resin in the absorbent structure is raised by decreasing the amount of the hydrophilic fibers (which have a small bulk density) and increasing the amount of the water-absorbent resin (which has excellent water absorbency and a large bulk density) as used. Thereby the thinning of the sanitary materials is aimed at without lowering the water absorption quantity.

(1) Liquid Permeability and Liquid Diffusibility:

However, the sanitary materials, in which the ratio of the hydrophilic fibers has been decreased and that of the water-absorbent resin has been increased in the above way, are in a favorable direction from the viewpoint of simple storage of liquids, but rather involve problems in the case of consideration of distribution and diffusion of the liquids under circumstances of actual use of diapers. The large amount of water-absorbent resin swells to become a soft gel due to water absorption to cause a phenomenon which is called "gel-blocking" that much hinders the permeation and diffusion of the liquids. Known examples of arts of improving these liquid permeability and liquid diffusibility include the following arts.

There is known a method in which there is used a hydrogel-formable absorbent polymer of which: the saline flow conductivity (SFC) value is at least about 30 ($10^{-7} \cdot cm^3 \cdot s \cdot g^{-1}$); the capacity value of performance under pressure (PUP) is at least 23 g/g under a closing pressure of 0.7 psi (5 kPa); and the basis weight is at least about 10 gsm (patent document 1).

There is known an absorbent structure of which: the water-absorbent resin concentration is at least 40 mass %; the saline flow conductivity (SFC) value is at least about 30 ($10^{-7} \cdot cm^3 \cdot s \cdot g^{-1}$); and the capacity value of performance under pressure (PUP) is at least 23 g/g under a closing pressure of 0.7 psi (5 kPa) (patent document 2).

There is known a method in which: in an absorbent structure, a water-absorbent resin of which the gel layer permeability (GLP) is at least 4 ($10^{-7} \cdot g^{-1}$) is used for an upper layer, and a water-absorbent resin of which the absorption capacity under load (AAP) is at least 15 (g/g) under a load of 50 g/cm$^2$ is used for a lower layer (patent document 3).

There is known a method in which a polycation is covalently bonded to a water-absorbent resin (patent document 4).

There is known an absorbent material including a mixture of: a plurality of absorbent gel-formable particles including a water-insoluble and water-swellable polymer; and an absorbency-improving polymer which is reactable with at least one component contained in urine (patent document 5).

There is known a method in which there is used a mixture of a spherical water-absorbent resin and a non-spherical water-absorbent resin (patent document 6).

There is known a method in which there is used a water-absorbent resin of which the saline flow conductivity (SFC) value is at least 5 ($10^{-7} \cdot cm^3 \cdot s \cdot g^{-1}$) and which contains a permeability-keeping agent (patent document 7).

There is known an absorbent structure having a division surrounded by a continuous area of a hydrogel absorbent polymer (patent document 8).

There is known a hydrogel-formable absorbent polymer of which: the dynamic gelation rate is at least about 0.18 g/g/sec; and the ability value of performance under pressure (PUP) is at least about 25 g/g under a binding pressure of 0.7 psi (5 kPa); wherein the hydrogel-formable absorbent polymer has a mass-median particle size of at least about 100 µm when the hydrogel-formable absorbent polymer exists in the form of particles (patent document 9).

There is known a water-absorbent material, in the rear half portion of which there is placed 55 to 100%, favorably 60 to 90%, of the entire mass of an absorbent gelling material (patent document 10).

There is known an absorbent member having a liquid-acquiring zone (patent document 11).

There is known a water-absorbent resin of which: the absorption capacity under load is not less than 30 g/g; and the gel layer liquid permeation rate is not more than 100 seconds (patent document 12).

There is known a process including the step of grinding crosslink-polymerized particles until their bulk density increases to not less than 0.72 g/ml (patent document 13).

There is known a process in which a water-absorbent resin is surface-treated with a surface-treating agent including a polyol and a cation (patent document 14).

There is known a process in which a water-absorbent resin is surface-treated with a surface-treating agent including an organic crosslinking compound (except polyols) and a cation (patent document 15).

There is known a water-swellable polymer as crosslinked with an unsaturated amino alcohol (patent document 16).

There is known a hydrogel-formable polymer of which: the saline flow conductivity (SFC) is at least 40 ($10^{-7} \cdot cm^3 \cdot s \cdot g^{-1}$); the AUL is at least 20 g/g under 0.7 psi (4826.5 Pa); and the Frangibility Index (FI) is at least 60% (patent document 17).

There is known a water-insoluble and water-swellable hydrogel which is coated with steric or electrostatic spacers and of which: the AUL is at least 20 g/g under 0.7 psi; and the gel strength is at least 1,600 Pa (patent document 18).

However, in cases where the above prior water-absorbent resins as disclosed in patent documents 1 to 18 have high liquid permeability, spaces between swollen gel particles increase to bring about deterioration of the capillary suction force. The deterioration of the capillary suction force is a cause that a residual liquid remaining not taken into the water-absorbent resin increases on surface layers of the sanitary materials to thus bring about: deterioration of the dry-touch property; an unpleasant feeling during wearing; and skin diseases such as skin eruption. In order to avoid such problems to maintain absorption properties of the absorbent structure, the ratios of the hydrophilic fibers and the water-absorbent resin are axiomatically limited, so a limit occurs also to the thinning of the sanitary materials.

That is to say, in the prior arts, the liquid permeability is pursued, but, to the capillary suction force as lost thereby, there has been paid no attention. In addition, in the prior arts, though the particle diameter distribution is a very important factor for the liquid permeation and the capillary suction force, yet, about it, there has been made no detailed explanation of the relationship of the particle diameter distribution with the liquid permeability and the capillary suction force. As matters now stand, almost no detailed explanation is made particularly also about a particle diameter distribution which is excellent in both of the liquid permeability and the capillary suction force or about a means for achieving such a particle diameter distribution.

(2) Particle Diameters:

In addition, such as the following arts are known as examples of water-absorbent resins having a controlled particle diameter distribution and arts in which particle diameter distributions of water-absorbent resins are controlled.

There is known an absorbent article including a high-molecular gelling agent having a mass-median particle diameter of 400 to 700 μm (patent document 19).

There is known a hydrogel polymer of which: the average particle diameter is in the range of 100 to 600 μm; and the logarithmic standard deviation σζ of the particle diameter distribution is not more than 0.35 (patent document 20).

There are known polymer material particles which are water-insoluble, absorbent, and formable into a hydrogel, and of which at least 80% are particles of such a size as passes through a sieve having a mesh opening size of 297 μm and is captured on a sieve having a mesh opening size of 105 μm (patent document 21).

There are known water-absorbent resin particles which have a specific surface area of 50 to 450 $m^2/g$ and contain a fine powder of hydrophilic silicon dioxide having a hydrophilicity of not less than 70% (patent document 22).

However, as to the above arts cited in such as patent documents 19 to 22, none of them is an art for achieving a particle diameter distribution specified for obtaining a water-absorbing agent which is excellent in both of the liquid permeability and the capillary suction force. In addition, the ranges of the resultant particle diameter distributions are also broad, and the absorption capacity without load and the absorption capacity under load are also different. Therefore, it has been difficult to obtain from the above arts the water-absorbing agent which is excellent in both of the liquid permeability and the capillary suction force.

[Patent document 1] WO 95/26209
[Patent document 2] EP 0951913
[Patent document 3] EP 0640330
[Patent document 4] WO 97/12575
[Patent document 5] WO 95/22356
[Patent document 6] WO 98/06364
[Patent document 7] WO 2001/066056
[Patent document 8] WO 97/25013
[Patent document 9] WO 98/47454
[Patent document 10] WO 96/01608
[Patent document 11] WO 97/34558
[Patent document 12] JP-A-089527/2001 (Kokai)
[Patent document 13] EP 1029886
[Patent document 14] WO 2000/53644
[Patent document 15] WO 2000/53664
[Patent document 16] U.S. Pat. No. 6,087,450
[Patent document 17] U.S. Pat. No. 6,414,214
[Patent document 18] US 2002/128618
[Patent document 19] U.S. Pat. No. 5,051,259
[Patent document 20] EP 0349240
[Patent document 21] EP 0579764
[Patent document 22] EP 0629411

As to the aforementioned prior art water-absorbent resins and/or water-absorbing agents of such as patent documents 1 to 22, the liquid permeability is improved, but, at the same time, the performance deterioration such as capillary suction force deterioration is caused. Thereby, the diffusibility and the liquid permeability in a water-absorbent structure which is a component material for such as sanitary materials are improved, but, on the other hand, there is caused the performance deterioration such that the dryness property and the liquid-retaining ability are deteriorated. Therefore, the aforementioned prior art ones have not necessarily been satisfactory ones. That is to say, there have occurred problems such that, even if either one of the performances is enhanced, the other performance is deteriorated. In order to solve such problems, it has been expected that there appears a water-absorbing agent which combines both performances of the liquid permeability and the capillary suction force.

DISCLOSURE OF THE INVENTION

Object of the Invention

That is to say, an object of the present invention is to provide a water-absorbing agent which combines both performances of the capillary suction force and the liquid permeability.

SUMMARY OF THE INVENTION

The present inventors diligently studied to solve the aforementioned problems. As a result, they have found out that the following six points are important for achieving the aforementioned object.

(1) The mass-average particle diameter is regulated to around 300 μm, and the particle diameter distribution denoted by the logarithmic standard deviation of the particle diameter distribution is controlled in a specific range.

The liquid permeability and the capillary suction force have properties contrary to each other, and their respective performances change greatly at around 300 μm as a boundary. Therefore, the water-absorbing agent which combines both performances of the liquid permeability and the capillary suction force can be obtained by specifying the mass-average particle diameter and the logarithmic standard deviation of the particle diameter distribution in the aforementioned ranges.

(2) The absorption capacity without load is not less than 15 g/g (favorably in the range of 15 to 33 g/g (but not including 33 g/g), more favorably in the range of 17 to 31 g/g (but not including 31 g/g), still more favorably in the range of 19 to 29 g/g (but not including 29 g/g), most favorably in the range of 23 to 28 g/g (but not including 28 g/g)).

In the case where the CRC is less than 15 g/g, the absorption capacity without load is too low and therefore unfavorable for practical use. In addition, particularly when the CRC is in the range of less than 33 g/g (favorably less than 29 g/g), the liquid-permeability-enhancing agent (β) remarkably takes effect.

(3) The water-extractable component content is not higher than 15 mass %.

In the case where the water-extractable component content is higher than 15 mass % in the present invention, there is a possibility not only that no effects of the present invention may be obtained, but also that the performance may be deteriorated in the use for water-absorbent structures. In addition, such a water-extractable component content is unfavorable also from the viewpoint of safety. As a cause of the performance deterioration, it can be cited that, when the water-absorbing agent absorbs water to swell, a high-molecular component elutes from the inside of the water-absorbing agent to thereby hinder the liquid permeation.

(4) The liquid permeability is enhanced by containing the liquid-permeability-enhancing agent (β).

Because the liquid permeability is enhanced by containing the liquid-permeability-enhancing agent (β), the water-absorbing agent which combines both performances of the liquid permeability and the capillary suction force can be obtained.

(5) Surfaces of water-absorbent resin particles are crosslink-treated.

In the case where surfaces of water-absorbent resin particles are not crosslink-treated, there is a possibility that the liquid permeability and the capillary suction force may greatly be damaged.

(6) There is possessed the shape of irregularly pulverized particles having a larger surface area than such as spherical shape.

By shaping the irregularly pulverized particles, the capillary suction force becomes higher in performance, so that the water-absorbing agent which combines both performances of the liquid permeability and the capillary suction force can be obtained.

By satisfying these conditions, the water-absorbing agent which combines both performances of the capillary suction force and the liquid permeability can be obtained wherein such a water-absorbing agent has hitherto never been.

In addition, it is favorable that at least a portion of water-absorbent resin particles (α) included in the water-absorbing agent have a porous structure.

That is to say, a water-absorbing agent according to the present invention has the following constitution.

A water-absorbing agent, which is a particulate water-absorbing agent comprising water-absorbent resin particles (α) and a liquid-permeability-enhancing agent (β), wherein the water-absorbent resin particles (α) are further-surface-crosslink-treated irregular-shaped pulverized particles of a crosslinked polymer of a monomer including acrylic acid and/or its salt;

wherein the particulate water-absorbing agent has:

a mass-average particle diameter (D50) in the range of 234 to 394 μm, a logarithmic standard deviation (σζ) of a particle diameter distribution in the range of 0.25 to 0.45, an absorption capacity without load (CRC) of not less than 15 g/g, and a water-extractable component content of not higher than 15 mass %; and further a liquid-permeability-enhancing agent (β) content in the range of 0.01 to 5 mass parts per 100 mass parts of the water-absorbent resin particles (α).

EFFECTS OF THE INVENTION

According to the present invention, the water-absorbing agent which combines both performances of the liquid permeability and the capillary suction force (such a water-absorbing agent has hitherto never been) can be provided by: surface-crosslinking the water-absorbent resin particles to such a degree that they will display the specific absorption capacity, wherein the water-absorbent resin particles have the specific mass-average particle diameter and the specific logarithmic standard deviation of the particle diameter distribution; and containing the liquid-permeability-enhancing agent (β).

EXPLANATION OF THE SYMBOLS

Figure 1:
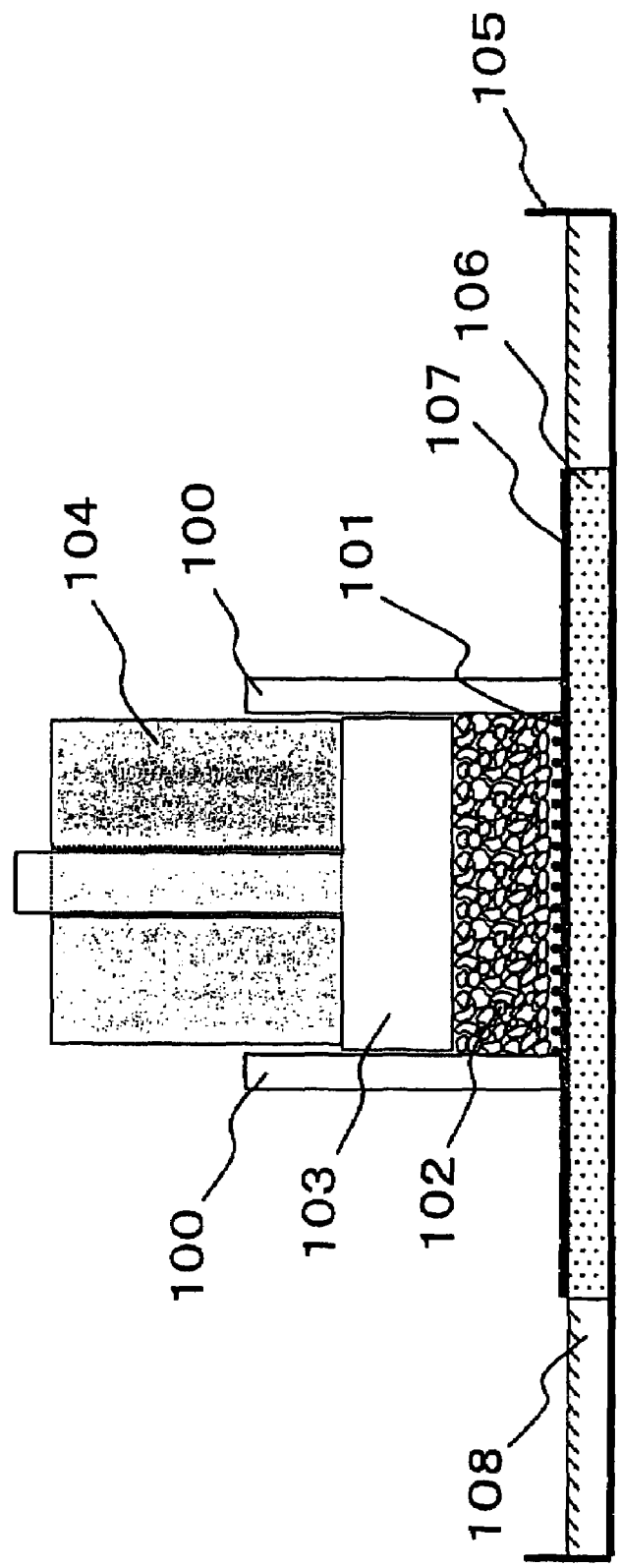
FIG. 1 is a schematic sectional view of a measurement apparatus as used for measuring the absorption capacity under load (AAP) for the 0.90 mass % physiological saline solution under a load of 4.83 kPa in 60 minutes.

100: Plastic supporting cylinder
101: Stainless metal gauze of 400 meshes
102: Swollen gel
103: Piston
104: Load (weight)
105: Petri dish 106: Glass filter plate
107: Filter paper
108: 0.90 mass % physiological saline solution
31: Tank
32: Glass tube
33: 0.69 mass % physiological saline solution
34: L-tube having cock
35: Cock
40: Receptacle
41: Cell
42: Stainless metal gauze
43: Stainless metal gauze
44: Swollen gel
45: Glass filter
46: Piston
47: Holes in piston
48: Collecting receptacle
49: Balance
1: Porous glass plate
2: Glass filter
3: Conduit
4: Liquid storage container
5: Supporting ring
6: 0.90 mass % physiological saline solution
7: Balance
8: Stand
9: Specimen to be measured (water-absorbent resin particles or absorbing agent)
10: Load (0.41 kPa (0.06 psi))
11: Air-intake pipe

DETAILED DESCRIPTION OF THE INVENTION

First of all, the abbreviations as hereinafter used are defined.

The CRC refers to the absorption capacity without load.

The SFC refers to the saline flow conductivity for a 0.69 mass % physiological saline solution.

The CSF refers to the capillary absorption capacity for a 0.90 mass % physiological saline solution.

The AAP refers to the absorption capacity under load.

The D50 refers to the mass-average particle diameter.

The $\sigma\zeta$ refers to the logarithmic standard deviation of the particle diameter distribution.

The physiological saline solution refers to an aqueous sodium chloride solution.

Hereinafter, the present invention is described in detail. Incidentally, hereinafter, the water-absorbing agent (favorably, a water-absorbent resin composition comprising the water-absorbent resin particles ($\alpha$) and the liquid-permeability-enhancing agent ($\beta$)) in the present invention refers to a material which comprises a water-absorbent resin having a crosslinked structure (hereinafter referred to simply as water-absorbent resin) as a main component (favorably in an amount of 50 to 100 mass % (or weight %: in the present invention, the weight and the mass have the same meaning, and their uses herein are unified into the mass), more favorably 80 to 100 mass %, still more favorably 90 to 100 mass %), wherein the water-absorbent resin is further modified (favorably surface-modified, particularly surface-crosslink-treated) with a crosslinking agent, and wherein the water-absorbing agent is modified by further comprising another component.

Hereinafter, in the present invention, the acid-group-containing water-absorbent resin particles are referred to as water-absorbent resin particles (a). Of such water-absorbent resin particles (a), those of which the particle diameters are controlled in the limited range, for example, those which have the mass-average particle diameter in the range of 234 to 394 µm and the $\sigma\zeta$ in the range of 0.25 to 0.45, are referred to as water-absorbent resin particles (a1). In addition, water-absorbent resin particles which are further-surface-crosslink-treated irregular-shaped pulverized particles of a crosslinked polymer of a monomer including acrylic acid and/or its salt are referred to as water-absorbent resin particles ($\alpha$).

(1) Process for Production of Water-Absorbent Resin Particles (a1):

The water-absorbent resin, usable in the present invention, refers to a hitherto known water-absorbent resin, for example, a hitherto publicly known crosslinked polymer which absorbs water in a large amount of essentially not smaller than 5 times, favorably in the range of 50 to 1,000 times, of the own weight in ion-exchanged water to thus form an anionic, nonionic, or cationic water-insoluble hydrogel.

This is generally a particulate water-absorbing agent of which the main component is a water-absorbent resin having a crosslinked structure obtained by a process including the step of polymerizing an unsaturated monomer component (favorably, an acid-group-containing (particularly, carboxyl-group-containing) unsaturated monomer), wherein the water-absorbent resin is obtained by a process including the steps of carrying out the above polymerization in a state of a monomer solution (favorably, an aqueous monomer solution), and then, if necessary, drying the resultant polymer, and then usually pulverizing the polymer before and/or after the drying step. Examples of such a water-absorbent resin include one or two or more of such as: partially-neutralized polymers of poly (acrylic acids); hydrolyzed graft polymers of starch-acrylonitrile; graft polymers of starch-acrylic acid; saponified copolymers of vinyl acetate-acrylic acid ester; hydrolyzed copolymers of acrylonitrile or acrylamide, or crosslinked polymers of these hydrolyzed copolymers; modified polymers of carboxyl-group-containing crosslinked polyvinyl alcohols; and crosslinked copolymers of isobutylene-maleic anhydride.

As to the water-absorbent resin, one kind of water-absorbent resin or a mixture of water-absorbent resins is used. Above all, an acid-group-containing water-absorbent resin is favorable, and one kind of carboxyl-group-containing water-absorbent resin (which is a carboxylic acid or its salt)) or a mixture of such resins is more favorable. Typically, there is favorably used a polymer which is obtained by a process including the step of crosslink-polymerizing a monomer including acrylic acid and/or its salt (neutralized material) as the main component, that is, a crosslinked poly(acrylic acid) (salt) polymer which contains a grafted component if necessary.

In addition, the above water-absorbent resin needs to be water-swellable and water-insoluble. The water-extractable component (water-soluble polymer) content of the water-absorbent resin as used is favorably not higher than 50 mass %, more favorably not higher than 25 mass %/o, still more favorably not higher than 20 mass %, yet still more favorably not higher than 15 mass %, particularly favorably not higher than 10 mass %.

As examples of the above acrylic acid salt, there can be cited such as: alkaline metal (e.g. sodium, potassium, lithium) salts, ammonium salts, and amine salts of acrylic acid. The above water-absorbent resin favorably contains, as its constitutional units, acrylic acid in the range of 0 to 50 mol % and an acrylic acid salt in the range of 100 to 50 mol % (wherein the total of both is not more than 100 mol %), more favorably, acrylic acid in the range of 10 to 40 mol % and an acrylic acid salt in the range of 90 to 60 mol % (wherein the total of both is not more than 100 mol %). Incidentally, the molar ratio between these acid and salt is referred to as neutralization degree. The neutralization of the water-absorbent resin for forming the above salt may be carried out in a monomer state before the polymerization, or may be carried out in a polymer state on the way of or after the polymerization, or may be carried out both in these states.

The monomer to obtain the water-absorbent resin as used in the present invention may further include monomers other than the above acrylic acid (salt) when the occasion demands. There is no especial limitation on the monomers other than the acrylic acid (salt). However, specific examples thereof include: anionic unsaturated monomers (e.g. methacrylic acid, maleic acid, vinylsulfonic acid, styrenesulfonic acid, 2-(meth)acrylamido-2-methylpropanesulfonic acid, 2-(meth)acryloylethanesulfonic acid, 2-(meth)acryloylpropanesulfonic acid) and their salts; nonionic-hydrophilic-group-containing unsaturated monomers (e.g. acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine, N-vinylacetamide); and cationic unsaturated monomers (e.g. N,N-dimethylaminoethyl(meth)acrylate, N,N-diethylaminoethyl(meth)acrylate, N,N-dimethylaminopropyl(meth)acrylate, N,N-dimethylaminopropyl (meth)acrylamide, and their quaternary salts). These monomers may be used either alone respectively or in appropriate combinations with each other.

In the present invention, when the monomers other than the acrylic acid (salt) are used, the ratio of these monomers other than the acrylic acid (salt) is favorably not more than 30 mol %, more favorably not more than 10 mol %, relative to the total of the acrylic acid and/or its salt used as the main component. If the above monomers other than the acrylic acid (salt) are used in the above ratio, then the absorption properties of the water-absorbent resin (water-absorbing agent) as finally obtained are still more enhanced, and further, the water-absorbent resin (water-absorbing agent) can be obtained at still lower costs.

When the above monomer is polymerized in order to obtain the water-absorbent resin as used in the present invention, it is possible to carry out bulk polymerization or precipitation polymerization. However, from the viewpoints of the performance, the facility of polymerization control, and further the absorption properties of a swollen gel, it is favorable to carry out aqueous solution polymerization or reversed-phase suspension polymerization in which the above monomer is used in the form of an aqueous solution. Such polymerization methods have hitherto been known in public and are disclosed in such as U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076, and EP 1178059. Incidentally, in the case where the above monomer is used in the form of an aqueous solution, the concentration of the monomer in this aqueous solution (hereinafter referred to as aqueous monomer solution) depends on the temperature of the aqueous solution or the kind of the monomer and is therefore not especially limited. However, this concentration is favorably in the range of 10 to 70 mass %, more favorably 20 to 60 mass %. In addition, when the above aqueous solution polymerization is carried out, a solvent other than water may be used jointly therewith if necessary. The kind of this solvent which is jointly used is not especially limited.

Examples of the method for the aqueous solution polymerization include: a method in which the aqueous monomer solution is polymerized while the resulting gel is crushed in a twin-arm type kneader; and a method in which the aqueous monomer solution is supplied into a predetermined container or onto a moving belt to carry out the polymerization and then the resultant gel is pulverized with such as a meat chopper.

When the above polymerization is initiated, there can be used, for example, the following: radical polymerization initiators such as potassium persulfate, ammonium persulfate, sodium persulfate, t-butyl hydroperoxide, hydrogen peroxide, and 2,2'-azobis(2-amidinopropane)dihydrochloride; and photoinitiators such as 2-hydroxy-2-methyl-1-phenyl-propan-1-one.

Furthermore, a redox initiator is also available by using the above polymerization initiator jointly with a reducing agent which promotes the decomposition of the above polymerization initiator and thus combining both with each other. Examples of the above reducing agent include: (bi)sulfurous acid (salts) such as sodium sulfite and sodium hydrogensulfite; L-ascorbic acid (salts); reducible metals (salts) such as ferrous salts; and amines. However, there is no especial limitation thereto.

The amount of the above polymerization initiator as used is favorably in the range of 0.001 to 2 mol %, more favorably 0.01 to 0.1 mol %. In the case where the amount of the above polymerization initiator as used is smaller than 0.001 mol %, there are disadvantages in that: the amount of unreacted monomers increases, and therefore the amount of residual monomers increases in the resultant water-absorbent resin or water-absorbing agent. On the other hand, in the case where the amount of the above polymerization initiator as used is larger than 2 mol %, there may be disadvantages in that the water-extractable component content in the resultant water-absorbent resin or water-absorbing agent increases.

In addition, the initiation of the polymerization reaction may be carried out by irradiating the reaction system with active energy rays such as radiations, electron rays, and ultraviolet rays. Furthermore, the above polymerization initiator may be used jointly therewith. Incidentally, the reaction temperature in the above polymerization reaction is not especially limited. However, the reaction temperature is favorably in the range of 10 to 130° C., more favorably 15 to 120° C., particularly favorably 20 to 100° C. In addition, the reaction duration or polymerization pressure is also not especially limited, but may be set appropriately for such as the kind of the monomer or polymerization initiator and the reaction temperature.

The aforementioned water-absorbent resin may be a self-crosslinked-type water-absorbent resin obtained without any crosslinking agent, but it is preferably a water-absorbent resin obtained by copolymerization or reaction with a crosslinking agent having at least two polymerizable unsaturated groups and/or at least two reactive groups per molecule (internal-crosslinking agent for water-absorbent resins) or with a crosslinking agent which is a cyclic compound and will have at least two reactive groups per molecule by its ring-opening reaction.

Specific examples of these internal-crosslinking agents include: N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether; polyhydric alcohols such as ethylene glycol, polyethylene glycol, propylene glycol, 1,3-butanediol, 1,4-butanediol, glycerol, and pentaerythritol; and ethylenediamine, ethylene carbonate, propylene carbonate, polyethyleneimine, and glycidyl(meth)acrylate.

These internal-crosslinking agents may be used either alone respectively or in appropriate combinations with each other. In addition, these internal-crosslinking agents may be added to the reaction system either in a lump or divisionally. In the case where at least one or two or more kinds of internal-crosslinking agents are used, it is favorable, in consideration of such as absorption properties of the finally obtained water-absorbent resin or water-absorbing agent, that a compound having at least two polymerizable unsaturated groups is essentially used during the polymerization.

The amount of the above internal-crosslinking agent as used is favorably in the range of 0.001 to 2 mol %, more favorably 0.02 to 1.0 mol %, still more favorably 0.06 to 0.30 mol %, particularly favorably 0.03 to 0.15 mol %, relative to the aforementioned monomer (exclusive of the internal-crosslinking agents). In the case where the amount of the above internal-crosslinking agent as used is smaller than 0.001 mol % or larger than 2 mol %, there is a possibility that no sufficient absorption properties can be obtained.

In the case where the above internal-crosslinking agent is used to introduce a crosslinked structure into the inside of the polymer, it is enough that the above internal-crosslinking agent is added to the reaction system before, on the way of, or after the polymerization of the above monomer, or after its neutralization. However, it is favorable to carry out the addition before the polymerization.

Incidentally, when the above polymerization is carried out, to the reaction system there can be added such as: hydrophilic polymers (e.g. starch, cellulose, starch derivatives, cellulose derivatives, polyvinyl alcohol, poly(acrylic acid) (salts), and crosslinked poly(acrylic acid) (salts)) in an amount of 0 to 50 mass % (relative to the monomer); and others (e.g. various foaming agents such as (hydrogen)carbonates, carbon dioxide, azo compounds, and inert organic solvents; various surfactants; chelating agents; chain transfer agents such as hypophosphorous acid (salts); inorganic fine particles such as kaolin, talc, and silicon dioxide; polyvalent metal salts such as poly(aluminum chloride), aluminum sulfate, and magnesium sulfate) in an amount of 0 to 10 mass % (relative to the monomer).

When the above crosslinked polymer is a gel as obtained by the aqueous solution polymerization, namely, a crosslinked hydrogel polymer, then the crosslinked polymer is dried, if necessary, and usually pulverized before and/or after this drying, thus forming the water-absorbent resin particles (a). In addition, the drying is carried out in the temperature range of usually 60 to 250° C., favorably 100 to 220° C., more favorably 120 to 200° C. The drying duration depends on the surface area and water content of the polymer and the kind of the dryer and is selected for the water content to be an objective one.

The water content of the water-absorbent resin usable in the present invention (defined as the amount of water contained in the water-absorbent resin and measured by the drying loss at 180° C. in 3 hours) is not especially limited. However, the water content is favorably such that the water-absorbent resin can be flowable even at room temperature, such as in the form of particles, a powder, or a particulate dried material agglomerate, and is more favorably such that the water-absorbent resin can be in a powder state having a water content of 0.2 to 30 mass %, still more favorably 0.3 to 15 mass %, particularly favorably 0.5 to 10 mass %. In the case where the water content is high, there is a possibility not only that the flowability may be so poor as to hinder the production, but also that the water-absorbent resin cannot be pulverized or controlled to the specific particle diameter distribution.

In addition, examples of the water-absorbent resin usable in the present invention include those which are of the irregular shape and easy to pulverize, such as in the form of particles, a powder, or a particulate dried material agglomerate.

The water-absorbent resin in the form of particles, a powder, or a particulate dried material agglomerate, which is obtained by the aforementioned process, is pulverized with a pulverizer. The water-absorbent resin particles (a) or (a1) can be obtained by the pulverization. Although not especially limited, examples of usable pulverizers include roll type pulverizers (e.g. roll mills), hammer type pulverizers (e.g. hammer mills), impact type pulverizers, cutter mills, turbo grinders, ball mills, and flash mills. Of these, the roll mills are favorable for controlling the particle diameter distribution. The pulverization may be carried out continuously twice or more for controlling the particle diameter distribution. However, the number of times of the pulverization is favorable 3 or more. In the case where the pulverization is carried out twice or more, the pulverizer as used each time may be either the same or different. It is also possible to use different ends of pulverizers in combination.

The pulverized water-absorbent resin particles (a) may be classified with a sieve of a specific mesh opening size in order to control the resin particles (a) to the specific particle diameter distribution. Although not especially limited, examples of classifiers as used include shaking sieves (e.g. unbalanced-weight driving types, resonance types, shaking motor types, electromagnetic types, circular shaking types), in-plane motion sieves (e.g. horizontal motion types, horizontal circle-straight line motion types, three-dimensional circular motion types), movable-mesh type sieves, forced-stirring type sieves, mesh-face-shaking type sieves, wind power sieves, and sound wave sieves. Favorably, the shaking sieves and the in-plane motion sieves are used. The sieve mesh opening size favorable for obtaining the water-absorbent resin particles (a1) usable in the present invention is in the range of 1,000 to 300 μm, more favorably 900 to 400 μm, most favorably 710 to 450 μm. Out of these ranges, there is a possibility that the objective particle diameter distribution cannot be obtained.

For the purpose of controlling the water-absorbent resin particles (a) usable in the present invention to the specific particle diameter distribution, the water-absorbent resin particles (a) usable in the present invention may be further classified to thereby remove a portion or all of particles smaller than a specific particle diameter. Although not especially limited, examples of classifiers as favorably used in this step include the aforementioned exemplifying ones. Besides them, such as fine-powder type classification apparatuses (e.g. centrifugal force types, inertial force types) are used. In this step, a portion or all of particles having particle diameters favorably smaller than 200 μm, more favorably smaller than 150 μm, most favorably smaller than 106 μm, are removed in order to obtain the water-absorbent resin particles (a1) usable in the present invention.

In addition, in the present invention, favorably, there may be involved a agglomeration step in which the particles as removed by the aforementioned classification are regenerated as larger particles or a particulate agglomerate by such as agglomeration to thus enable their or its use as the water-absorbent resin particles (a1) usable in the present invention.

In this agglomeration step, publicly known arts to regenerate a fine powder are usable. Examples of such usable arts include methods in which: warm water and a fine powder of a water-absorbent resin are mixed together and then dried (U.S. Pat. No. 6,228,930); a fine powder of a water-absorbent resin is mixed with an aqueous monomer solution, and then the resultant mixture is polymerized (U.S. Pat. No. 5,264,495); water is added to a fine powder of a water-absorbent resin, and then the resultant mixture is agglomerated under not less than a specific face pressure (EP 0844270); a fine powder of a water-absorbent resin is sufficiently wetted to form an amorphous gel, and then this gel is dried and pulverized (U.S. Pat. No. 4,950,692); and a fine powder of a water-absorbent resin and a polymer gel are mixed together (U.S. Pat. No. 5,478,879). However, there is favorably used the aforementioned method in which warm water and a fine powder of a water-absorbent resin are mixed together and then dried. In addition, the water-absorbent resin obtained from the agglomeration step may be either used, as it is, as the water-absorbent resin particles (a1) usable in the present invention, or returned to the aforementioned pulverization step and/or classification step. However, for obtaining the objective water-absorbent resin particles (a1), the return to the pulverization step and/or classification step is favorable. The water-absorbent resin particles (a), as regenerated in this way, substantially have a porous structure. The ratio of the water-absorbent resin, as regenerated in the agglomeration step and contained in the water-absorbent resin particles (a1) usable in the present invention, is favorably not less than 10 mass %, more favorably not less than 15 mass %, most favorably not less than 20 mass %. In the case where used as the water-absorbent resin particles (a1) usable in the present invention, the water-absorbent resin as regenerated in the agglomeration step has a larger surface area and therefore gives a larger capillary suction force than a unregenerated water-absorbent resin and is thus advantageous over it in performance.

(2) Features of Water-Absorbent Resin Particles (a1):

The water-absorbent resin particles (a1) usable in the present invention have the following features.

Examples of the shape of the water-absorbent resin particles (a1) usable in the present invention include spherical shape, fibrous shape, bar shape, approximately spherical shape, flat shape, irregular shape, agglomerated particle shape, and porous particle shape without being especially limited. However, the irregularly pulverized shape as obtained via the pulverization step is favorably usable. In addition, favorably, the water-absorbent resin particles (a1) usable in the present invention partially contain the particles having a porous structure (which may be a foamed structure) and the water-absorbent resin particles (a) as regenerated in the aforementioned agglomeration step, and their ratio is favorably not less than 10 mass %, more favorably not less than 15 mass %, most favorably not less than 20 mass %. Furthermore, the bulk density (defined by JIS K-3362) of the water-absorbent resin particles (a1) is favorably in the range of 0.40 to 0.90 g/ml, more favorably 0.50 to 0.80 g/ml, from the viewpoint of excellent properties of the water-absorbing agent.

As to the particle diameters of the water-absorbent resin particles (a1) usable in the present invention, there are favorably used those which have a mass-average particle diameter in the range of favorably 10 to 1,000 μm, more favorably 100 to 800 μm, still more favorably 200 to 400 μm, particularly favorably 250 to 380 μm.

As to the water-absorbent resin particles (a1) usable in the present invention, the mass ratio (particles having particle diameters of not smaller than 300 μm)/(particles having particle diameters of smaller than 300 μm) is favorably in the range of 80/20 to 20/80, more favorably 78/22 to 30/70, particularly favorably 75/25 to 40/60.

Favorable ranges of the particle diameter distribution are hereinafter shown further in addition to the above.

The mass ratio (particles having particle diameters of smaller than 300 μm but not smaller than 150 μm)/(particles having particle diameters of smaller than 150 μm) is favorably in the range of 100/0 to 50/50, more favorably 99.5/0.5 to 65/35, particularly favorably 99/1 to 75/25.

The mass ratio (particles having particle diameters of not smaller than 500 μm)/(particles having particle diameters of smaller than 500 μm but not smaller than 300 μm) is favorably in the range of 60/40 to 0/100, more favorably 50/50 to 0/100, particularly favorably 40/60 to 0/100.

The water-absorbent resin particles (a1) usable in the present invention are favorably regulated to the aforementioned particle diameter distribution, whereby there can be obtained the water-absorbing agent according to the present invention which is excellent in both of the liquid permeability and the capillary suction force.

Incidentally, the "particles having particle diameters of not smaller than 300 μm", as referred to in the present invention, refers to particles remaining on a mesh of the mesh opening size of 300 μm as measured after having been classified by the below-mentioned classification method. In addition, the "particles having particle diameters of smaller than 300 μm" similarly refers to particles having passed through the mesh of the mesh opening size of 300 μm as measured after having been classified by the below-mentioned classification method. The same reference is applied also to the other mesh opening sizes (e.g. 850 μm, 710 μm, 600 μm, 500 μm, 425 μm, 212 μm, 200 μm, 150 μm, 45 μm). Incidentally, for example, in the case where 50 mass % of particles are classified with the mesh of the mesh opening size of 300 μm, the mass-average particle diameter (D50) is 300 μm.

The water-absorbent resin particles (a1), as obtained by the above process, display an absorption capacity without load in the range of favorably 15 to 50 g/g, more favorably 20 to 40 g/g, most favorably 25 to 35 g/g, for a 0.9 mass % physiological saline solution without load. The properties such as this absorption capacity without load are adjusted appropriately for the purpose. However, in the case where this absorption capacity without load is less than 15 g/g or more than 50 g/g, there is a possibility that the water-absorbing agent according to the present invention cannot be obtained.

The water-absorbent resin particles (a1), as obtained by the above process, have a crosslinked structure. The water-extractable component content of the water-absorbent resin particles as used is favorably not higher than 25 mass %, more favorably not higher than 20 mass %, still more favorably not higher than 15 mass %, particularly favorably not higher than 10 mass %. The water-extractable component content of the water-absorbent resin particles is measured by the below-mentioned method.

(3) Process for Production of Water-Absorbing Agent:

The water-absorbing agent used in the present invention is favorably obtained by a process including the steps of: crosslink-treating surfaces of the water-absorbent resin particles (a1), as obtained by the aforementioned process, with a specific surface-crosslinking agent; and adding the liquid-permeability-enhancing agent (β).

Favorably, the surface-crosslinking is carried out to such a degree that the absorption capacity without load (CRC) will be in the range of 15 to 33 g/g (but not including 33 g/g) and that the absorption capacity under load (AAP) will be in the range of 15 to 29 g/g.

As examples of surface-crosslinking agents as favorably used in the present invention, there can be cited compounds which have at least two functional groups reactable with a functional group of the water-absorbent resin (wherein the at least two functional groups are, favorably, functional groups which can make a dehydration reaction or transesterification reaction with a carboxyl group). The functional group of the water-absorbent resin is favorably an anionic dissociating group and more favorably the carboxyl group.

Examples of such a surface-crosslinking agent include:

polyhydric alcohol compounds (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol);

epoxy compounds (e.g. ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol); polyamine compounds (e.g. ethylenediamine, diethylenetriamine, triethylenetetramine, tetraethylenepentaamine, pentaethylenehexamine, and polyethyleneimine) and their inorganic or organic salts (e.g. azetidinium salts);

polyisocyanate compounds (e.g. 2,4-tolylene diisocyanate and hexamethylene diisocyanate);

aziridine compounds (e.g. polyaziridine);

polyoxazoline compounds (e.g. 1,2-ethylenebisoxazoline, bisoxazoline, and polyoxazoline);

carbonic acid derivatives (e.g. urea, thiourea, guanidine, dicyandiamide, 2-oxazolidinone);

alkylene carbonate compounds (e.g. 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one);

haloepoxy compounds (e.g. epichlorohydrin, epibromohydrin, and α-methylepichlorohydrin) and their polyamine addition products (e.g. Kymene (registered trademark) produced by Hercules);

oxetane compounds;

silane coupling agents (e.g. γ-glycidoxypropyltrimethoxysilane and γ-aminopropyltriethoxysilane); and polyvalent metallic compounds (e.g. hydroxides or chlorides or sulfates or nitrates or carbonates of such as zinc, calcium, magnesium, aluminum, iron and zirconium). These may be used either alone respectively or in combinations with each other.

In addition, the amount of the above surface-crosslinking agent as used is favorably in the range of 0.001 to 10 mass parts, more favorably 0.01 to 5 mass parts, per 100 mass parts of the water-absorbent resin particles (a1). In the case where this amount is larger than 10 mass parts, not only are there economical disadvantages in that no performance corresponding thereto is obtained, but also the surface-crosslinking agent remains unfavorably in a large amount. Furthermore, in the case where this amount is smaller than 0.001 mass part, there is a possibility that the resultant saline flow conductivity (SFC) for a 0.69 mass % physiological saline solution may be insufficient.

In addition, such as inorganic acids and organic acids may be used in order to more accelerate the reaction of the surface-crosslinking agent to thus more enhance the absorption properties. Examples of these inorganic acids and organic acids include sulfuric acid, phosphoric acid, hydrochloric acid, citric acid, glyoxylic acid, glycolic acid, glycerol phosphate, glutaric acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidinoacetic acid, malic acid, isethionic acid, citraconic acid, adipic acid, itaconic acid, crotonic acid, oxalic acid, salicylic acid, gallic acid, sorbic acid, gluconic acid, and p-toluenesulfonic acid. In addition, there may be used those which are disclosed in EP 0668080, such as inorganic acids, organic acids, and polyamino acids. The amount of these materials as used differs according to such as pH of the water-absorbent resin, but is favorably in the range of 0 to 10 mass parts, more favorably 0.1 to 5 mass parts, per 100 mass parts of the water-absorbent resin particles (a1).

In the present invention, when the water-absorbent resin particles (a1) and the surface-crosslinking agent are mixed together, water is favorably used as a solvent. The amount of water, as used, depends upon such as type or particle diameters of the water-absorbent resin particles (a1), but is favorably larger than 0 mass part but not larger than 20 mass parts, more favorably in the range of 0.5 to 10 mass parts, still more favorably 0.5 to 5 mass parts, per 100 mass parts of the solid content of the water-absorbent resin particles (a1).

In addition, when the water-absorbent resin particles (a1) and the surface-crosslinking agent are mixed together, a hydrophilic organic solvent may be used as a solvent, if necessary. Examples of the hydrophilic organic solvent include: lower alcohols (e.g. methyl alcohol, ethyl alcohol, n-propyl alcohol, isopropyl alcohol, n-butyl alcohol, isobutyl alcohol, and t-butyl alcohol); ketones (e.g. acetone); ethers (e.g. dioxane, tetrahydrofuran, and alkoxypolyethylene glycol); amides (e.g. N,N-dimethylformamide); and sulfoxides (e.g. dimethyl sulfoxide). The amount of the hydrophilic organic solvent, as used, depends upon such as type or particle diameters of the water-absorbent resin particles (a1), but is favorably not larger than 20 mass parts, more favorably not larger than 10 mass parts, still more favorably not larger than 5 mass parts, per 100 mass parts of the solid content of the water-absorbent resin particles (a1).

In addition, when the water-absorbent resin particles (a1) and the surface-crosslinking agent are mixed together, there may be caused to coexist a noncrosslinkable water-soluble inorganic base (favorably: alkaline metal salts, ammonium salts, alkaline metal hydroxides, water-soluble aluminum salts, ammonia or its hydroxide) and an irreducible alkaline-metal-salt pH buffer (favorably such as hydrogencarbonates, dihydrogenphosphates, and hydrogenphosphates) for the purpose of more uniformly mixing the water-absorbent resin particles (a1) and the surface-crosslinking agent together. The amount of these materials, as used, depends upon such as type or particle diameters of the water-absorbent resin particles (a1), but is favorably in the range of 0.005 to 10 mass parts, more favorably 0.05 to 5 mass parts, per 100 mass parts of the solid content of the water-absorbent resin particles (a1).

In addition, when the water-absorbent resin particles (a1) are mixed with the surface-crosslinking agent, for example, there may be used a method in which: the water-absorbent resin particles (a1) are dispersed into the above hydrophilic organic solvent, and then the surface-crosslinking agent is added to the resultant dispersion. However, in a favorable method, the surface-crosslinking agent, which is dissolved or dispersed in water and the hydrophilic organic solvent if necessary, is spraywise or dropwise added directly to the water-absorbent resin particles (a1) under stirring. In addition, when the mixing is carried out with water, there may be made to coexist such as a water-insoluble inorganic fine particle powder, a water-soluble polyvalent metal, or a surfactant.

A mixing apparatus, as used when the water-absorbent resin particles (a1) and the surface-crosslinking agent are mixed together, has great mixing power favorably for uniformly and surely mixing both. Favorable examples of the above mixing apparatus include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, and screw type extruders.

After the water-absorbent resin particles (a1) and the surface-crosslinking agent have been mixed together, the resultant mixture is subjected to the heat treatment and light irradiation treatment, whereby surfaces of the water-absorbent resin particles (a1) are crosslinked. Favorably, this surface-crosslinking is carried out to such a degree that the absorption capacity without load (CRC) will be in the range of 15 to 33 g/g (but not including 33 g/g) and that the absorption capacity under load (AAP) will be in the range of 15 to 29 g/g. When the heat treatment is carried out in the present invention, the treating time is favorably in the range of 1 to 180 minutes, more favorably 3 to 120 minutes, still more favorably 5 to 100 minutes. The treating temperature is favorably in the range of 60 to 250° C., more favorably 100 to 210° C., still more favorably 120 to 200° C. In the case where the heating temperature is lower than 60° C., there is a possibility not only that the heat treatment may take so much time as to cause the lowering of the productivity, but also that no uniform crosslinking may be achieved and therefore no objective water-absorbing agent can be obtained. In addition, in the case where the heating temperature is higher than 250° C., the resultant surface-crosslink-treated water-absorbent resin particles ($\alpha$) are damaged and therefore there are cases where it is difficult to obtain the water-absorbing agent which is excellent in the absorption capacity.

The aforementioned heat treatment can be carried out with conventional dryers or heating furnaces. Examples of the above dryers include channel type mixing dryers, rotary dryers, disk dryers, fluidized-bed dryers, air blow type dryers, and infrared dryers. In the case where the light irradiation treatment is carried out in place of the heat treatment in the present invention, it is favorable to irradiate ultraviolet rays, and besides, photoinitiators are usable.

In the case where the water-absorbent resin particles (a1) have been heated in the aforementioned surface treatment step, it is favorable to cool the heated water-absorbent resin particles. It is favorable that the cooling is carried out until the temperature falls into the range of 100 to 20° C. In addition, examples of coolers as used for the cooling include apparatuses in which the heating media of the above dryers as used for the heat treatment are replaced with cooling media.

As to the water-absorbing agent as obtained via the aforementioned steps, its particle diameter distribution is favorably regulated by the particle regulation step.

If necessary, the above process for production of the water-absorbing agent according to the present invention may further comprise a step for providing the water-absorbing agent or water-absorbent resin particles with various functions, for example, a step of adding such as: deodorants; antibacterial agents; perfumes; foaming agents; pigments; dyes; hydrophilic short fibers; plasticizers; pressure-sensitive adhesives; metal soap; surfactants; manure; oxidants; reducing agents; water; salts; chelating agents; fungicides; hydrophilic polymers (e.g. polyethylene glycol); paraffins; hydrophobic polymers; thermoplastic resins (e.g. polyethylene, polypropylene); and thermosetting resins (e.g. polyester resins, urea resins). The amount of these additives as used is favorably in the range of 0 to 10 mass parts, more favorably 0 to 1 mass part, per 100 mass parts of the water-absorbing agent.

The liquid-permeability-enhancing agent ($\beta$), as referred to in the present invention, refers to a substance such that the SFC of the water-absorbing agent as obtained by mixing the surface-crosslink-treated water-absorbent resin particles ($\alpha$) and the liquid-permeability-enhancing agent ($\beta$) together can be higher than the SFC of the water-absorbent resin particles ($\alpha$) to which the liquid-permeability-enhancing agent ($\beta$) is not added. The addition of the liquid-permeability-enhancing agent ($\beta$) may be carried out any time of before, during, and after the surface treatment. The liquid-permeability-enhancing agent ($\beta$) has an effect of enhancing the liquid permeability by spreading the spaces between swollen water-absorbent resin particles due to such as a role like a spacer or an ionic surface-crosslinking effect. On the other hand, the liquid-permeability-enhancing agent ($\beta$) further has an effect of deteriorating the capillary suction force. However, surprisingly, the water-absorbing agent according to the present invention, which has been controlled to the specific range of particle diameter distribution, is excellent in the liquid permeability and the capillary suction force, and therefore can maintain high capillary suction force though it contains the liquid-permeability-enhancing agent ($\beta$). In addition, surprisingly, in the case where the water-absorbing agent according to the present invention, which has been controlled to the specific range of particle diameter distribution, contains the liquid-permeability-enhancing agent ($\beta$), its liquid-permeability-enhancing effect is much higher than conventional. That is to say, usually, the SFC varies greatly with the particle diameter distribution. Specifically, as the average particle diameter becomes smaller, the SFC value becomes smaller. However, the present inventors have discovered a feature that the SFC of the water-absorbing agent which contains the liquid-permeability-enhancing agent ($\beta$) depends only on the CRC regardless of the particle diameter distribution of the water-absorbing agent if this particle diameter distribution is in a certain specific range. On the other hand, the CSF of the water-absorbing agent which contains the liquid-permeability-enhancing agent ($\beta$) depends on the particle diameter distribution. Therefore, for the water-absorbing agent, which has been controlled to a certain specific particle diameter distribution, to contain the liquid-permeability-enhancing agent ($\beta$) has made it possible to obtain the water-absorbing agent which is excellent in both of the SFC and CSF.

Examples of the liquid-permeability-enhancing agent ($\beta$), as used in the present invention, include hydrophilic inorganic compounds, and there are favorably used such as water-insoluble hydrophilic inorganic fine particles and water-soluble polyvalent metal salts. As to the hydrophilicity as referred to in the present invention, for example, there can be cited those which have a hydrophilicity of not less than 70% as disclosed in EP 0629411. In the present invention, such as cationic high-molecular compounds (e.g. those which are cited as examples on column 11 of U.S. Pat. No. 5,797,893) and hydrophobic inorganic fine particles enhance the liquid permeability, but increase the contact angle of the water-absorbing agent to bring about great deterioration of the CSF. Therefore, as the case may be, it is unfavorable that they are used. Such a surfactant as deteriorates the surface tension of the water-absorbing agent brings about great deterioration of the CSF. Therefore, it is unfavorable that such a surfactant is used in the present invention.

In the case where the liquid-permeability-enhancing agent ($\beta$) as used in the present invention is in the form of inorganic fine particles, their particle diameters are favorably not larger than 500 μm, more favorably not larger than 100 μm, most favorably not larger than 10 μm, from the viewpoint of the handling property and the addition effects. The aforementioned particle diameters include both a case of particle diameters of primary particles and a case of particle diameters of secondary particles (agglomerated materials, agglomerates). In the case where particles of compounds of which the particles have high hardness and are not easily destroyed by impact, such as silica and alumina that are non-agglomerates (primary particles), are used, the particle diameters of primary particles of the agglomerates or agglomerated materials are favorably not larger than 5 μm, more favorably not larger than 1 μm, most favorably not larger than 0.1 μm.

Specific examples of these liquid-permeability-enhancing agents ($\beta$) as used in the present invention include: mineral products such as talc, kaolin, fuller's earth, bentonite, activated clay, barite, natural asphaltum, strontium ore, ilmenite, and pearlite; aluminum compounds such as aluminum sulfate tetradeca- to octadecahydrates (or anhydride), potassium aluminum sulfate dodecahydrate, sodium aluminum sulfate dodecahydrate, ammonium aluminum sulfate dodecahydrate, aluminum chloride, poly(aluminum chloride), and aluminum oxide; other polyvalent metal salts, polyvalent metal oxides, and polyvalent metal hydroxides; hydrophilic amorphous silica (e.g. dry method: Reolosil QS-20 of Tokuyama Corporation, precipitation method: Sipernat 22S and Sipernat 2200 of DEGUSSA Corporation); and oxide composites such as silicon oxide-aluminum oxide-magnesium oxide composite (Attagel #50 of ENGELHARD Corporation), silicon oxide-aluminum oxide composite, and silicon oxide-magnesium oxide composite. In addition, those which are cited as examples in such as U.S. Pat. No. 5,164,459 and EP 0761241 are also usable. It is favorable that the hydrophilic particles (e.g. aluminum sulfate tetradeca- to octadecahydrates and the hydrophilic amorphous silica) are selected from among the above particles and used. However, in the case where the hydrophilicity of the particles is low, it is enough to use particles obtained by treating surfaces of particles with hydrophilic compounds to thus hydrophilize them. These may be used either alone respectively or in combinations with each other.

As to methods for mixing the liquid-permeability-enhancing agent ($\beta$) as used in the present invention, the mixing is carried out by such as: a method in which the water-soluble polyvalent metal salt (e.g. aluminum sulfate) and the cationic high-molecular compound is mixed in the form of an aqueous solution, a slurry, or a powder. However, a favorable method is the method in which the mixing is carried out in the form of a powder. In addition, the amount of the addition is favorably in the range of 0.01 to 5 mass %, more favorably 0.05 to 3 mass %, relative to the water-absorbent resin particles. In the case where the amount of the addition is larger than 5 mass %, there is a possibility that the absorption capacity may be deteriorated. In the case where the amount of the addition is smaller than 0.01 mass %, there is a possibility that it may become impossible to obtain the effects of the addition. In addition, by changing the amount of the addition, it is possible to adjust the liquid permeability and capillary suction force of the water-absorbing agent.

An apparatus for mixing the water-absorbent resin particles and the liquid-permeability-enhancing agent ($\beta$) together does not need to have especially great mixing power. For example, the mixing may be carried out with such as disintegrators or sieving machines. Favorable examples of the above mixing apparatus include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, screw type extruders, and static mixers. In addition, the time of the addition may be any time of before the water-absorbing agent is obtained, during, and after its production in the aforementioned production process. However, the time of the addition is favorably after the surface-crosslinking.

The water-absorbing agent, as obtained in the above way, favorably has such as the following CRC, AAP, SFC, CSF, particle diameter distribution, surface tension, contact angle, bulk density, water-extractable component content, shape, and water content. However, the water-absorbing agent according to the present invention may be obtained by other processes.

Besides, in the present invention, it is also possible to provide the water-absorbing agent according to the present invention with various functions by further adding such as: disinfectants; deodorants; antibacterial agents; perfumes; various inorganic powders; foaming agents; pigments; dyes; hydrophilic short fibers; manure; oxidants; reducing agents; water; and salts.

(4) Features of Water-Absorbing Agent According to Present Invention:

The water-absorbing agent according to the present invention has the following features.

The water-absorbing agent according to the present invention is a particulate water-absorbing agent comprising the water-absorbent resin particles ($\alpha$) and the liquid-permeability-enhancing agent ($\beta$), wherein the water-absorbent resin particles ($\alpha$) are obtained by a process including the step of crosslink-polymerizing a monomer including acrylic acid and its salt and have a crosslinked structure.

The water-absorbing agent according to the present invention includes particles having been surface-crosslink-treated with the compound which has at least two functional groups reactable with a functional group of the water-absorbent resin (wherein the at least two functional groups are, favorably, functional groups which can make a dehydration reaction or transesterification reaction with a carboxyl group).

The water-absorbing agent according to the present invention exhibits an absorption capacity without load (CRC) of at least not less than 15 g/g, favorably in the range of 15 to 33 g/g (but not including 33 g/g), more favorably 17 to 31 g/g (but not including 31 g/g), still more favorably 19 to 29 g/g (but not including 29 g/g), most favorably 23 to 28 g/g (but not including 28 g/g), for a 0.9 mass % physiological saline solution without load. In the case where the CRC is less than 15 g/g, not only is there a possibility that the absorption capacity may be too low to obtain sufficient performance in the case of the use for such as water-absorbent structures, but also there are economical disadvantages. In addition, in the case where the CRC is not less than 33 g/g, there a possibility that: because the gel absorption capacity may be too high and because the gel strength may accordingly be deteriorated, the enhancement of the liquid permeability (enhancement of SFC) by the liquid-permeability-enhancing agent (β) may be insufficient to obtain the objective performances. The liquid-permeability-enhancing agent (β), as contained in the water-absorbing agent according to the present invention, has effects particularly when the CRC is less than 33 g/g and has great effects when the CRC is less than 29 g/g.

The particle diameter distribution of the water-absorbing agent according to the present invention is favorably substantially the same as that of the aforementioned water-absorbent resin particles (a1). The water-absorbing agent according to the present invention is characterized by combining performances excellent in both of the liquid permeability and the capillary suction force. Needed for achieving this is the strictly controlled particle diameter distribution. The present inventors have discovered that the liquid permeability and the capillary suction force change greatly at around 300 μm in particle diameter as a boundary, and thus the present inventors have utilized it for the present invention. That is to say, particles having particle diameters larger than around 300 μm as a boundary display high liquid permeability, but are inferior in the capillary suction force, while particles having particle diameters smaller than around 300 μm as a boundary are excellent in the capillary suction force, but their liquid permeability is greatly deteriorated. The present inventors have completed the present invention by discovering that, if the above-discovered fact is utilized to regulate the mass-average particle diameter (D50) to around 300 μm and to control the logarithmic standard deviation (σζ) of the particle diameter distribution in the specific range and further if the liquid-permeability-enhancing agent (β) is made to be contained, then it becomes possible to obtain the water-absorbing agent which combines performances excellent in both of the liquid permeability and the capillary suction force.

The particle diameter distribution of the water-absorbing agent according to the present invention is specifically as follows.

As to the water-absorbing agent according to the present invention, the mass-average particle diameter (D50) is favorably in the range of 234 to 394 μm, more favorably 256 to 363 μm, most favorably 281 to 331 μm. As to the liquid permeability and the capillary suction force, these performances change greatly at around 300 μm in particle diameter as a boundary. Smaller particle diameters are advantageous to the capillary suction force, but disadvantageous to the liquid permeability. In addition, larger particle diameters are advantageous to the liquid permeability, but disadvantageous to the capillary suction force. That is to say, in the case where the mass-average particle diameter (D50) is not larger than 233 μm or not smaller than 395 μm, there is a possibility that the objective water-absorbing agent according to the present invention, which is excellent in both of the liquid permeability and the capillary suction force, cannot be obtained, and that, accordingly, a water-absorbing agent which is excellent in only either one of them may be obtained.

As to the water-absorbing agent according to the present invention, the logarithmic standard deviation (σζ) of the particle diameter distribution is favorably in the range of 0.25 to 0.45, more favorably 0.27 to 0.43, most favorably 0.30 to 0.40. The smaller logarithmic standard deviation (σζ) of the particle diameter distribution shows the narrower particle diameter distribution. However, it is important for the water-absorbing agent according to the present invention that the particle diameter distribution has the broadness in some degree. In the case where the logarithmic standard deviation (σζ) of the particle diameter distribution is less than 0.25, not only is the capillary suction force deteriorated, but also the productivity is greatly deteriorated. In the case where the logarithmic standard deviation (σζ) of the particle diameter distribution is more than 0.45, there is a possibility that the particle diameter distribution may be too broad, thus resulting in low liquid permeability. In addition, the water-absorbing agent according to the present invention includes particles having particle diameters in the range of 200 μm above and below 300 μm (i.e. 100 to 500 μm) in an amount of favorably not smaller than 80 mass %, more favorably not smaller than 85 mass %, relative to the water-absorbing agent.

As to the water-absorbing agent according to the present invention, the mass ratio (particles having particle diameters not smaller than 300 μm)/(particles having particle diameters smaller than 300 μm) is favorably in the range of 80/20 to 20/80, more favorably 78/22 to 30/70, particularly favorably 75/25 to 40/60.

Favorable ranges of the particle diameter distribution are hereinafter shown further in addition to the above.

The mass ratio (particles having particle diameters smaller than 300 μm but not smaller than 150 μm)/(particles having particle diameters smaller than 150 μm) is favorably in the range of 100/0 to 50/50, more favorably 99.5/0.5 to 65/35, particularly favorably 99/1 to 75/25.

The mass ratio (particles having particle diameters not smaller than 500 μm)/(particles having particle diameters smaller than 500 μm but not smaller than 300 μm) is favorably in the range of 60/40 to 0/100, more favorably 50/50 to 0/100, particularly favorably 40/60 to 0/100.

The water-absorbing agent according to the present invention is favorably regulated to the aforementioned particle diameter distribution and thereby can have performances excellent in both of the liquid permeability and the capillary suction force.

As the water-absorbing agent according to the present invention, there are used those of which the water-extractable component content is favorably not higher than 15 mass %, more favorably not higher than 13 mass %, most favorably not higher than 10 mass %. In addition, particularly when the water-extractable component content of the water-absorbing agent is not higher than 15 mass %, the liquid-permeability-enhancing agent (β) usable in the present invention remarkably takes effect. In the case where the water-extractable component content is higher than 15 mass % in the present invention, there is a possibility not only that no effects of the present invention may be obtained, but also that the performance may be deteriorated in the use for water-absorbent structures. In addition, such a water-extractable component content is unfavorable also from the viewpoint of safety. As a cause of the performance deterioration, it can be cited that, when the water-absorbing agent absorbs water to swell, a high-molecular component elutes from the inside of the water-absorbing agent to thereby hinder the liquid permeation. The high-molecular component can be considered to resist when a liquid flows across surfaces of water-absorbing agent particles. In addition, similarly, the elution of the high-molecular component has a possibility of increasing the viscosity of an absorbed solution to thus deteriorate the capillary suction force. The water-extractable component content of the water-absorbing agent is measured by the below-mentioned method.

As to the water-absorbing agent according to the present invention, it is favorable that a portion of the water-absorbent resin particles (α) included in the water-absorbing agent have a porous structure (which may be a foamed structure). The phrase "have a porous structure", as hereupon referred to, refers to a state such as where fine particles of the water-absorbent resin particles (α) are agglomerated or bubbles are contained in an amount of not smaller than 10% of the volume. In addition, it is more favorable that this porous structure is a structure obtained by the aforementioned agglomeration step. Above all, it is the most favorable that the porous structure is that of a fine-particles-agglomerated material obtained by a process as disclosed in U.S. Pat. No. 6,228,930. The ratio of the water-absorbent resin particles (α) having the porous structure is favorably not less than 10 mass %, more favorably not less than 15 mass %, most favorably not less than 20 mass %.

As to the water-absorbing agent according to the present invention, the saline flow conductivity (SFC) for a 0.69 mass % physiological saline solution is favorably not less than 50 ($10^{-7} \cdot cm^3 \cdot s \cdot g^{-1}$), more favorably not less than 70 ($10^{-7} \cdot cm^3 \cdot s \cdot g^{-1}$), most favorably not less than 100 ($10^{-7} \cdot cm^3 \cdot s \cdot g^{-1}$). In the case where the SFC is less than 50 ($10^{-7} \cdot cm^3 \cdot s \cdot g^{-1}$), there is a possibility that the liquid permeability or liquid diffusibility may be insufficient in the use for water-absorbent structures. In addition, favorably, the upper limit value of the SFC is 500 ($10^{-7} \cdot cm^3 \cdot s \cdot g^{-1}$). The saline flow conductivity (SFC) for a 0.69 mass % physiological saline solution is measured by the below-mentioned measurement method.

As to the water-absorbing agent according to the present invention, the capillary absorption capacity (CSF) showing the capillary suction force for a 0.90 mass % physiological saline solution is favorably not less than 15 g/g, more favorably not less than 18 g/g, still more favorably not less than 20 g/g, most favorably not less than 23 g/g. In the case where the CSF is less than 15 g/g, there is a possibility that the dryness property or the liquid-retaining ability may be insufficient in the use as a portion of a water-absorbent structure. The capillary absorption capacity (CSF) for a 0.90 mass % physiological saline solution is measured by the below-mentioned measurement method.

The CSF of the water-absorbing agent according to the present invention is not a little influenced by the capillary force of the water-absorbing agent. The capillary force p of the water-absorbing agent has a property as shown by the following expression.

$$p \propto \gamma \cdot \cos \theta / Rc$$

wherein:

p: Capillary force of the water-absorbing agent

γ: Surface tension of the water-absorbing agent

θ: Contact angle of the water-absorbing agent

Rc: Value corresponding to the capillary radius depending on the particle diameter distribution of the water-absorbing agent.

As can be understood from the above expression, the capillary force p varies with the surface tension γ of the water-absorbing agent, the contact angle θ of the water-absorbing agent, and the value Rc corresponding to the capillary radius depending on the particle diameter distribution of the water-absorbing agent. That is to say, as the surface tension γ becomes larger, the capillary force p becomes larger. And, as the contact angle θ nears 0, the capillary force p becomes larger. Therefore, the surface tension γ and contact angle θ of the water-absorbing agent according to the present invention are favorably in the following ranges.

As to the water-absorbing agent according to the present invention, its surface tension is favorably not less than 30 (mN/m), more favorably not less than 50 (mN/m), most favorably not less than 70 (mN/m). In the case where the surface tension is less than 30 (mN/m), there is a possibility not only that the CSF may be deteriorated, but also that the objective performances cannot be obtained. The surface tension is measured by the below-mentioned measurement method.

As to the water-absorbing agent according to the present invention, its contact angle is favorably not more than 80°, more favorably not more than 50°, most favorably not more than 30°. In the case where the contact angle is more than 80°, there is a possibility not only that the CSF may be deteriorated, but also that the objective performances cannot be obtained. The contact angle is measured by the below-mentioned measurement method.

The water-absorbing agent according to the present invention combines excellent liquid permeability and capillary suction force. The liquid permeability and the capillary suction force has a correlation such that, if either one of them is enhanced, the other is deteriorated. However, the water-absorbing agent according to the present invention has excellent relations as have never been before. That is to say, the water-absorbing agent according to the present invention, favorably, satisfies the following relational expression:

$$SFC\ (10^{-7} \cdot cm^3 \cdot s \cdot g^{-1}) \geq \epsilon - 8 \times CSF\ (g/g)$$

wherein ε is a constant and ε=260

In addition, the water-absorbing agent according to the present invention, more favorably, satisfies the aforementioned expression when ε=270 and, most favorably, satisfies the aforementioned expression when ε=280.

That is to say, the water-absorbing agent according to the present invention is favorably a particulate water-absorbing agent comprising the water-absorbent resin particles (α) wherein the water-absorbent resin particles (α) are further-surface-crosslink-treated irregular-shaped pulverized particles of a crosslinked polymer of a monomer including acrylic acid and its salt;

wherein the particulate water-absorbing agent satisfies $$SFC\ (10^{-7} \cdot cm^3 \cdot s \cdot g^{-1}) \geq 260 - 8 \times CSF\ (g/g)$$

and has: an SFC in the range of 50 to 500 ($10^{-7} \cdot cm^3 \cdot s \cdot g^{-1}$), a mass-average particle diameter (D50) in the range of 234 to 394 μm and a logarithmic standard deviation (σζ) of a particle diameter distribution in the range of 0.25 to 0.45.

More favorably, the aforementioned water-absorbing agent further comprises the liquid-permeability-enhancing agent (β), and the liquid-permeability-enhancing agent (β) content is in the range of 0.01 to 5 mass parts per 100 mass parts of the water-absorbent resin particles (α).

Accordingly, the water-absorbing agent according to the present invention combines the liquid permeability and the capillary suction force and therefore, in diapers, can display excellent liquid diffusibility and further can decrease the wet-back amount. In addition, the water-absorbing agent according to the present invention can display the aforementioned features in diapers having high-concentration cores, particularly, in diapers having core concentrations of not less than 50 mass %.

As to the water-absorbing agent according to the present invention, the absorption capacity under load (AAP) for a 0.9 mass % physiological saline solution under 4.83 kPa in 60 minutes is favorably in the range of 15 to 29 g/g, more favorably 20 to 27 g/g.

Although not especially limited, the water content of the water-absorbing agent according to the present invention is favorably in the range of 0 to 400 mass %, more favorably 0.01 to 40 mass %, still more favorably 0.1 to 10 mass %.

The water-absorbing agent according to the present invention may be those which have a bulk density of less than 0.40 g/ml or more than 0.90 g/ml. However, the bulk density is favorably in the range of 0.40 to 0.90 g/mil, more favorably 0.50 to 0.80 g/ml (the method for measuring the bulk density is specified in JIS K-3362). In the case of water-absorbing agents which have a bulk density of less than 0.40 g/ml or more than 0.90 g/ml, there is a possibility that they may be damaged easily by the process and may accordingly be deteriorated in property.

(5) Process for Production of Water-Absorbent Structure and Water Absorption Properties:

The water-absorbing agent according to the present invention can be combined with an appropriate material and thereby formed into the water-absorbent structure which is, for example, favorable as an absorbent layer for sanitary materials. Hereinafter, a description is made about the water-absorbent structure.

The water-absorbent structure refers to a molded composition which comprises a water-absorbent resin or water-absorbing agent and another material and is used for sanitary materials (e.g. disposable diapers, sanitary napkins, incontinent pads, and medical pads) for absorption of such as blood, body fluids, and urine. Examples of the above other material include cellulose fibers. Specific examples of the cellulose fibers include: wood pulp fibers from wood, such as mechanical pulp, chemical pulp, semichemical pulp, and dissolving pulp; and synthetic cellulose fibers, such as rayon and acetate. Favorable cellulose fibers are the wood pulp fibers. These cellulose fibers may partially contain synthetic fibers such as nylon and polyester. When the water-absorbing agent according to the present invention is used as a portion of the water-absorbent structure, the mass of the water-absorbing agent according to the present invention as contained in the water-absorbent structure is favorably in the range of 20 to 100 mass %. In the case where the mass of the water-absorbing agent according to the present invention as contained in the water-absorbent structure is smaller than 20 mass %, there is a possibility that no sufficient effects can be obtained.

For the purpose of obtaining the water-absorbent structure from the water-absorbing agent (as obtained by the above process) and the cellulose fibers, for example, publicly known means for obtaining water-absorbent structures can appropriate be selected from among such as: a method in which the water-absorbing agent is spread onto paper or mat made of such as the cellulose fibers and is, if necessary, interposed therebetween; and a method in which the cellulose fibers and the water-absorbing agent are uniformly blended together. A favorable method is a method in which the water-absorbing agent and the cellulose fibers are mixed together in a dry manner and then compressed. This method can greatly prevent the water-absorbing agent from falling off from the cellulose fibers. The compression is favorably carried out under heating, and its temperature range is favorably the range of 50 to 200° C. In addition, for the purpose of obtaining the water-absorbent structure, methods as disclosed in JP-A-509591/1997 (Kohyo) and JP-A-290000/1997 (Kokai) are also favorably used.

In the case where used for water-absorbent structures, the water-absorbing agent according to the present invention is so good in the balance between the liquid permeability and the capillary suction force as to give water-absorbent structures which are very excellent in that they quickly take liquids in and further in that the amount of the liquids remaining on their surface layers is small.

In addition, because the above water-absorbing agent has these excellent water absorption properties, this water-absorbing agent can be used as water-absorbing and water-retaining agents for various purposes. For example, this water-absorbing agent can be used for such as: water-absorbing and water-retaining agents for absorbent articles (e.g. disposable diapers, sanitary napkins, incontinent pads, and medical pads); agricultural and horticultural water-retaining agents (e.g. substitutes for peat moss, soil-modifying-and-improving agents, water-retaining agents, and agents for duration of effects of agricultural chemicals); water-retaining agents for buildings (e.g. dew-condensation-preventing agents for interior wall materials, cement additives); release control agents; coldness-retaining agents; disposable portable body warmers; sludge-solidifying agents; freshness-retaining agents for foods; ion-exchange column materials; dehydrating agents for sludge or oil; desiccating agents; and humidity-adjusting materials. In addition, the water-absorbing agent as obtained in the present invention can be used particularly favorably for sanitary materials for absorption of excrement, urine, or blood, such as disposable diapers and sanitary napkins.

In the case where the water-absorbent structure is used for sanitary materials (e.g. disposable diapers, sanitary napkins, incontinent pads, and medical pads), this water-absorbent structure is used favorably with a constitution including: (a) a liquid-permeable top sheet placed so as to be adjacent to a wearer's body; (b) a liquid-impermeable back sheet placed so as to be adjacent to the wearer's clothes at a distance from the wearer's body; and (c) the water-absorbent structure placed between the top sheet and the back sheet. The water-absorbent structure may be in more than one layer or used along with such as a pulp layer.

In a more favorable constitution, the basis mass of the water-absorbing agent in the water-absorbent structure is favorably in the range of 60 to 1,500 g/m$^2$, more favorably 100 to 1,000 g/m$^2$, still more favorably 200 to 800 g/m$^2$.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to these Examples. The performances of the water-absorbent resin particles or water-absorbing agents were measured by the following methods. The following measurement was carried out under conditions of a room temperature (25° C.) and a humidity of 50 RH %.

Incidentally, in cases of water-absorbing agents having been used for end products such as sanitary materials, the water-absorbing agents have already absorbed moisture. Therefore, the measurement may be carried out after appropriately separating the water-absorbing agents from the end products and then drying the separated water-absorbing agents under a reduced pressure at a low temperature (e.g. under not higher than 1 mmHg at 60° C. for 12 hours). In addition, all the water-absorbing agents as used in the Examples and Comparative Examples of the present invention had water contents of not higher than 6 mass %.

(1) Absorption Capacity without Load (Absorption Capacity without Load/CRC for 0.90 Mass % Physiological Saline Solution without Load in 30 Minutes):

An amount of 0.20 g of water-absorbent resin particles or water-absorbing agent was uniformly placed and sealed into a bag (85 mm×60 mm) made of nonwoven fabric (trade name: Heatron Paper, type: GSP-22, produced by Nangoku Pulp Kogyo Co., Ltd.) and then immersed into a large excess (usually about 500 ml) of 0.9 mass % physiological saline solution of room temperature. After 30 minutes, the bag was pulled up and then drained of water by centrifugal force (as disclosed in edana ABSORBENCY II 441.1-99) with a centrifugal separator (produced by Kokusan Co., Ltd., centrifugal separator: model H-122) for 3 minutes, and then the mass W1 (g) of the bag was measured. In addition, the same procedure as the above was carried out without the water-absorbent resin particles or water-absorbing agent, and the resultant mass W0 (g) was measured. Then, the absorption capacity (g/g) without load was calculated from these W1 and W0 in accordance with the following equation:

Absorption capacity (g/g) without load=($W1$ (g)−$W0$ (g))/(mass (g) of water-absorbent resin particles or water-absorbing agent)−1

(2) Absorption Capacity Under Load (Absorption Capacity Under Load/AAP for 0.90 Mass % Physiological Saline Solution Under Load of 4.83 kPa in 60 Minutes):

The measurement was carried out with an apparatus as shown in FIG. 1.

A stainless metal gauze 101, which was a screen of 400 meshes (mesh opening size: 38 μm), was attached by fusion to a bottom of a plastic supporting cylinder 100 having an inner diameter of 60 mm. Then, under conditions of a room temperature (20 to 25° C.) and a humidity of 50 RH %, onto the above gauze, there was uniformly spread 0.90 g of water-absorbing agent 102, and further thereon, there were mounted a piston 103 and a load 104 in sequence, wherein the piston had an outer diameter of only a little smaller than 60 mm and made no gap with the inner wall surface of the supporting cylinder, but was not hindered from moving up and down, and wherein the piston and the load were adjusted so that a load of 4.83 kPa (0.7 psi) could uniformly be applied to the water-absorbing agent Then, the mass Wa (g) of the resultant one set of measurement apparatus was measured.

A glass filter plate 106 having a diameter of 90 mm (produced by Sogo Rikagaku Glass Seisakusho Co., Ltd., pore diameter: 100 to 120 μm) was mounted inside a Petri dish 105 having a diameter of 150 mm, and then a 0.90 mass % physiological saline solution 108 (20 to 25° C.) was added up to the same level as the top surface of the glass filter plate, on which a filter paper 107 having a diameter of 90 mm (produced by ADVANTEC Toyo Co., Ltd., trade name: (JIS P 3801, No. 2), thickness: 0.26 mm, diameter of captured particles: 5 μm) was then mounted so that its entire surface would be wetted, and further, an excess of liquid was removed.

The above one set of measurement apparatus was mounted on the above wet filter paper, thereby getting the liquid absorbed under the load. Then, 1 hour later, the one set of measurement apparatus was removed by being lifted to measure its mass Wb (g). Then, the absorption capacity (g/g) under load was calculated from the Wa and Wb in accordance with the following equation:

Absorption capacity (g/g) under load=($Wb$ (g)−$Wa$ (g))/mass ((0.9) g) of water-absorbing agent (3) Mass-Average Particle Diameter (D50) and Logarithmic Standard Deviation (σζ) of Particle Diameter Distribution:

Water-absorbent resin particles or water-absorbing agents were classified with JIS standard sieves having mesh opening sizes of such as 850 μm, 710 μm, 600 μm, 500 μm, 425 μm, 300 μm, 212 μm, 150 μm, and 45 μm. Then, the percentages R of the residues on these sieves were plotted on a logarithmic probability paper. Therefrom, a particle diameter corresponding to R=50 mass % was read as the mass-average particle diameter (D50). In addition, the logarithmic standard deviation (σζ) of the particle diameter distribution is shown by the following equation. The smaller σζ value shows the narrower particle diameter distribution.

σζ=0.5×ln($X2$/$X1$)

(wherein: X1 is a particle diameter when R=84.1%, and X2 is a particle diameter when R=15.9%)

As to the classification method for measuring the mass-average particle diameter (D50) and the logarithmic standard deviation (σζ) of the particle diameter distribution, 10.0 g of water-absorbent resin particles or water-absorbing agent was placed onto JIS standard sieves (having mesh opening sizes of 850 μm, 710 μm, 600 μm, 500 μm, 425 μm, 300 μm, 212 μm, 150 μm, and 45 μm) (THE IIDA TESTING SIEVE: diameter=8 cm) under conditions of a room temperature (20 to 25° C.) and a humidity of 50 RH %, and then classified with a shaking classifier (IIDA SIEVE SHAKER, TYPE: ES-65 type, SER. No. 0501) for 5 minutes.

(4) Saline Flow Conductivity (SFC) for 0.69 Mass % Physiological Saline Solution:

The saline flow conductivity (SFC) for a 0.69 mass % physiological saline solution is a value showing the liquid permeability displayed by the water-absorbing agent when it is swollen. The larger SFC value shows the higher liquid permeability.

The following test was carried out according to the saline flow conductivity (SFC) test as described in JP-A-509591/1997 (Kohyo).

Figure 2:
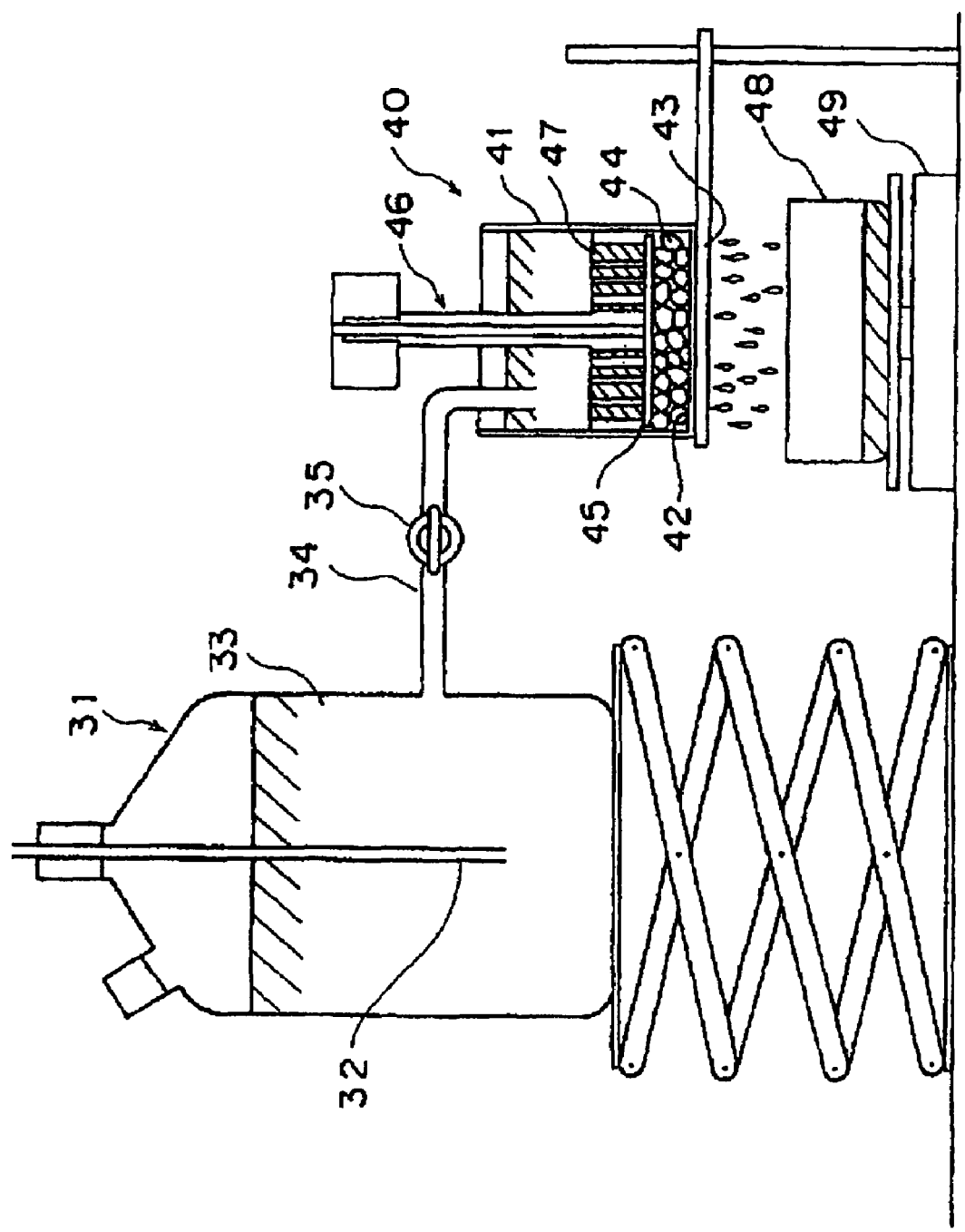
FIG. 2 is a schematic sectional view of a measurement apparatus as used for measuring the saline flow conductivity (SFC) for the 0.69 mass % physiological saline solution.

An apparatus as shown in FIG. 2 was used, and a water-absorbing agent (0.900 g) as uniformly placed in a receptacle 40 was swollen in synthetic urine (1) under a load of 0.3 psi (2.07 kPa) for 60 minutes, and the gel layer height of the resultant gel 44 was recorded. Next, under the load of 0.3 psi (2.07 kPa), a 0.69 mass % physiological saline solution 33 was passed through the swollen gel layer from a tank 31 under a constant hydrostatic pressure. This SFC test was carried out at room temperature (20 to 25° C.). The amount of the liquid passing through the gel layer was recorded as a function to time with a computer and a balance at twenty seconds' intervals for 10 minutes. The rate $F_s$ (t) of the flow passing through the swollen gel 44 (mainly between particles thereof) was determined in a unit of g/s by dividing the incremental mass (g) by the incremental time (s). The time when the constant hydrostatic pressure and the stable flow rate were obtained was represented by $t_s$, and only the data as obtained between $t_s$ and 10 minutes were used for the flow rate calculation. The $F_s$ (t=0) value, namely, the initial rate of the flow passing through the gel layer, was calculated from the flow rates as obtained between $t_s$ and 10 minutes. The $F_s$ (t=0) was calculated by extrapolating the results of a least-squares fit of $F_s$ (t) versus time to t=0.

Saline flow conductivity for 0.69 mass % physiological saline solution=($F_s$(t=0)×$L_0$)/(ρ×$A$×Δ$P$)=($F_s$(t=0)×$L_0$)/139,506 where:

$F_s$ (t=0): flow rate denoted by g/s;

$L_0$ initial thickness of gel layer denoted by cm;

ρ: density of NaCl solution (1.003 g/cm$^3$);

A: area of top of gel layer in cell 41 (28.27 cm$^2$);

ΔP: hydrostatic pressure applied to gel layer (4,920 dyne/cm$^2$); and the unit of the SFC value is: ($10^{-7} \cdot cm^3 \cdot s \cdot g^{-1}$).

As to the apparatus as shown in FIG. 2, a glass tube 32 was inserted in the tank 31, and the lower end of the glass tube 32 was placed so that the 0.69 mass % physiological saline solution 33 could be maintained at a height of 5 cm from the bottom of the swollen gel 44 in the cell 41. The 0.69 mass % physiological saline solution 33 in the tank 31 was supplied to the cell 41 through an L-tube 34 having a cock 35. A receptacle 48 to collect the passed liquid was placed under the cell 41, and this collecting receptacle 48 was set on a balance 49. The inner diameter of the cell 41 was 6 cm, and a No. 400 stainless metal gauze (mesh opening size: 38 μm) 42 was set at the bottom thereof. Holes 47 sufficient for the liquid to pass through were opened in the lower portion of a piston 46, and its bottom portion was equipped with a well-permeable glass filter 45 so that the water-absorbing agent or its swollen gel would not enter the holes 47. The cell 41 was placed on a stand to put the cell thereon. The face, contacting with the cell, of the stand was set on a stainless metal gauze 43 that did not inhibit the liquid permeation.

The synthetic urine (1) as used was obtained by mixing together the following: 0.25 g of calcium chloride dihydrate; 2.0 g of potassium chloride; 0.50 g of magnesium chloride hexahydrate; 2.0 g of sodium sulfate; 0.85 g of ammonium dihydrogenphosphate; 0.15 g of diammonium hydrogenphosphate; and 994.25 g of pure water.

(5) Capillary Absorption Capacity (CSF) for 0.90 Mass % Physiological Saline Solution:

The CSF is an index showing the capillary suction force of the water-absorbing agent.

Figure 3:
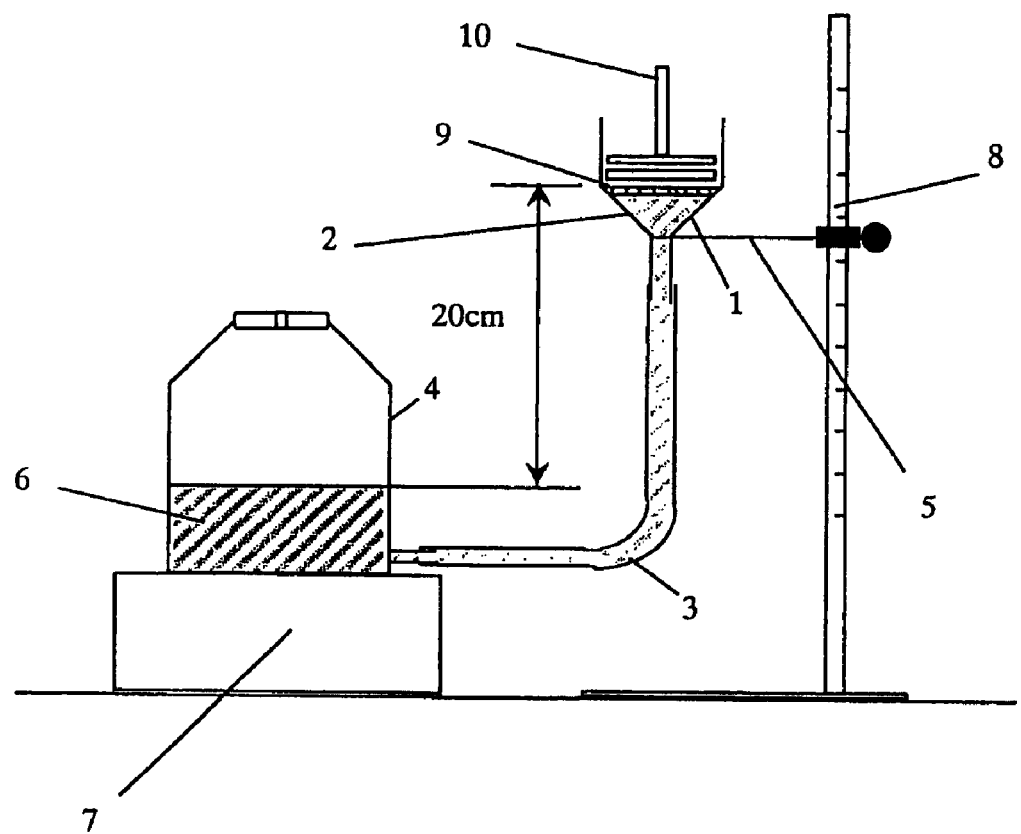
FIG. 3 is a schematic sectional view of a measurement apparatus as used for measuring the capillary absorption capacity (CSF) for the 0.90 mass % physiological saline solution.

The capillary absorption capacity in the present invention is determined by measuring the ability of the absorbent structure to absorb a liquid against a negative pressure gradient of the water column of 20 cm under a load of 0.06 psi within a predetermined time. While referring to FIG. 3, an apparatus and method for measuring the capillary absorption capacity are described.

A conduit 3 was connected to a lower portion of a glass filter 2 of 60 mm in diameter having a liquid-absorbing surface of a porous glass plate 1 (glass filter particle No. #3: Buchner type filter TOP 17G-3 (code no. 1175-03) produced by Sogo Rikagaku Glass Seisakusho Co., Ltd.), and this conduit 3 was connected to an opening as provided to a lower portion of a liquid storage container 4 of 10 cm in diameter. The porous glass plate of the aforementioned glass filter has an average pore diameter of 20 to 30 μm, and can retain water in the porous glass plate by its capillary force against the negative pressure of the water column even in a state where a difference of 60 cm between heights of liquid surfaces is made, so that a state of no introduction of air can be kept A supporting ring 5 was fitted to the glass filter 2 in order to let up and down its height, and the system was filled with a 0.90 mass % physiological saline solution 6, and the liquid storage container was put on a balance 7. After it had been confirmed that there was no air in the conduit and under the porous glass plate of the glass filter, the difference in height between a liquid surface level of the top of the 0.90 mass % physiological saline solution 6 in the liquid storage container 4 and a level of the upside of the porous glass plate 1 was adjusted to 20 cm, and then the glass filter was fixed to a stand 8.

An amount of 0.44 g of specimen to be measured 9 (water-absorbent resin particles or water-absorbing agent) was quickly dispersed uniformly onto the glass filter (porous glass plate 1) in the funnel, and further thereon a load 10 (0.06 psi) having a diameter of 59 mm was put, and then, 30 minutes later, there was measured a value (W20) of the 0.90 mass % physiological saline solution as absorbed by the specimen to be measured 9.

The capillary absorption capacity is determined from the following equation.

Capillary absorption capacity $D1$ (g/g) of water-absorbent resin particles or water-absorbing agent at height of 20 cm=absorption amount ($W20$) (g)/0.44 (g)

(6) Extractable (Water-Extractable) Component Content:

Into a plastic receptacle of 250 ml in capacity having a lid, 184.3 g of 0.90 mass % physiological saline solution was weighed out. Then, 1.00 g of water-absorbent resin particles or water-absorbing agent was added to this aqueous solution, and they were stirred for 16 hours, thereby the extractable component content in the resin was extracted. This extract liquid was filtrated with a filter paper (produced by ADVANTEC Toyo Co., Ltd., trade name: (JIS P 3801, No. 2), thickness: 0.26 mm, diameter of captured particles: 5 μm), and then 50.0 g of the resultant filtrate was weighed out and used as a measuring solution.

To begin with, only the 0.90 mass % physiological saline solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out for the measuring solution, thus obtaining titration amounts ([NaOH] ml and [HCl] ml).

For example, if the water-absorbent resin or water-absorbent resin particles or water-absorbing agent comprises acrylic acid and its sodium salt in known amounts, the extractable component content of the water-absorbent resin can be calculated from the average molecular weight of the monomers and the titration amounts, as obtained from the above procedures, in accordance with the following equation. In the case of unknown amounts, the average molecular weight of the monomers is calculated from the neutralization degree as determined by the titration.

Extractable component content (mass %)=0.1×(average molecular weight)×184.3×100×([HCl]−[$b$HCl])/1,000/1.0/50.0

Neutralization degree (mol %)=(1−([NaOH]−[$b$NaOH])/([HCl]−[$b$HCl]))×100

(7) Surface Tension:

Into a glass beaker of 120 ml, there was weighed out 80 ml of 0.90 mass % physiological saline solution. Then, 1.00 g of water-absorbing agent was added to this aqueous solution, and then they were mildly stirred for 5 minutes. After the stirring had been carried out for 1 minute, the surface tension of the resultant solution was measured by the plate method. The surface tension of the 0.90 mass % physiological saline solution to which no water-absorbing agent had been added was 72 (mN/m).

(8) Contact Angle:

A double-coated pressure-sensitive adhesive tape was stuck onto an SUS sheet, and then the water-absorbent resin particles or water-absorbing agent was spread onto this double-coated tape, and then the water-absorbent resin particles or water-absorbing agent which had not adhered to the double-coated tape was scraped off to prepare a specimen sheet of which the surface was covered with the water-absorbent resin particles or water-absorbing agent. When a 0.90 mass % physiological saline solution was made to contact with the above specimen sheet, the contact angle was measured by the sessile drop method with a contact angle meter (FACE CA-X model, produced by Kyowa Kaimen Kagaku K.K.) under conditions of 20° C. and 60% RH. The contact angle at 1 second later than dropping a liquid drop of the 0.90 mass % physiological saline solution onto the specimen sheet was measured 5 times per one specimen. Its average value was determined and taken as the contact angle of the water-absorbent resin particles or water-absorbing agent.

Example 1

(1) Polymerization

In a reactor as prepared by lidding a jacketed stainless twin-arm kneader of 10 liters in capacity having two sigma-type blades, there was prepared a reaction liquid by dissolving 9.36 g (0.08 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer (1) was taken out after 30 minutes from the start of the polymerization.

The crosslinked hydrogel polymer (1) as obtained above was in the form of finely divided pieces having diameters of not larger than about 5 mm. This finely divided crosslinked hydrogel polymer (1) was spread onto a metal gauze of 50 meshes (mesh opening size: 300 μm) and then hot-air-dried at 180° C. for 50 minutes, thus obtaining a water-absorbent resin (A1) which was of the irregular shape and easy to pulverize, such as in the form of particles, a powder, or a particulate dried material agglomerate.

(2) Pulverization and Classification

The resultant water-absorbent resin (A1) was pulverized with a roll mill and then further classified with a JIS standard sieve having a mesh opening size of 600 μm. Next, particles having passed through the 600 μm in the aforementioned operation were classified with a JIS standard sieve having a mesh opening size of 180 μm, whereby water-absorbent resin particles (B1F) passing through the JIS standard sieve having the mesh opening size of 180 μm were removed, thus obtaining water-absorbent resin particles (B1).

(3) Agglomeration of Fine Powder

Figure 4:
FIG. 4 is a view obtained by taking a photograph of the agglomerated water-absorbent resin particles (B1A) as obtained from Example 1.

The water-absorbent resin particles (B1F) having been removed in the above "(2) Pulverization and classification" were agglomerated according to the method of Granulation Example 1 as disclosed in U.S. Pat. No. 6,228,930. The resultant agglomerated material was pulverized and classified by the same procedure as of the aforementioned (2), thus obtaining agglomerated water-absorbent resin particles (B1A). A view obtained by taking a photograph of these agglomerated water-absorbent resin particles (B1A) is shown in FIG. 4. As seen therein, the water-absorbent resin particles (B1A) had a porous structure.

(4) Mixing of Fine-Powder-Agglomerated Product

An amount of 90 mass parts of the water-absorbent resin particles (B1) and 10 mass parts of the water-absorbent resin particles (B1A) were uniformly mixed together to obtain water-absorbent resin particles (B1A10). The CRC of the water-absorbent resin particles (B1A10) was 33.4 g/g.

(5) Surface Treatment

An amount of 100 g of the water-absorbent resin particles (B1A10) as obtained from the aforementioned step were mixed with a surface-treating agent comprising a mixed liquid of 1.0 g of 1,4-butanediol and 4.0 g of pure water, and then the resultant mixture was heat-treated at 195° C. for 20 minutes. Furthermore, the resultant particles were disintegrated to such a degree that they could pass through a JIS standard sieve having a mesh opening size of 600 μm. As a result, surface-crosslink-treated water-absorbent resin particles (C1-1A10) were obtained. The water-absorbent resin particles (C1-1A10) displayed a CRC of 28.3 g/g, an SFC of 50 ($10^{-7} \cdot cm^3 \cdot s \cdot g^{-1}$), and a CSF of 24.1 g/g.

Figure 5:
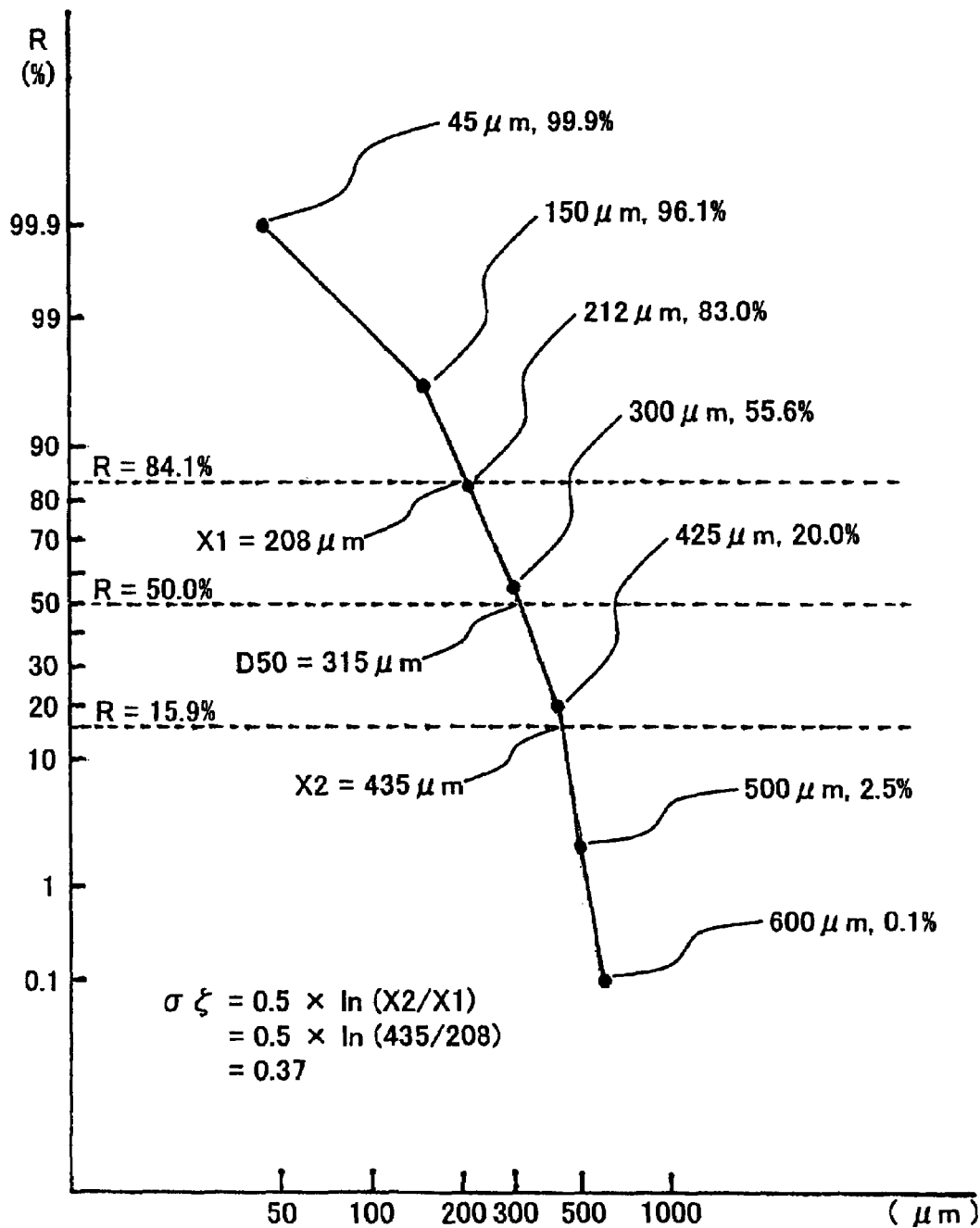
FIG. 5 is a diagram showing how the D50 and σζ of the water-absorbing agent (D1-1A10) were determined with a logarithmic normal probability paper

Next, 100 mass parts of the water-absorbent resin particles (C1-1A10) were uniformly mixed with 0.3 mass part of Reolosil QS-20 (hydrophilic amorphous silica produced by Tokuyama Corporation), thus obtaining a water-absorbing agent (D1-1A10). The resultant water-absorbing agent (D1-1A10) was also of the shape of a powder. The results of having measured its properties are shown in Tables 1, 2 and 3. In addition, a logarithmic normal probability paper as used to determine D50 and σζ is also shown in FIG. 5.

Example 2

An amount of 100 g of the water-absorbent resin particles (B1A10) as obtained from Example 1 were mixed with a surface-treating agent comprising a mixed liquid of 0.5 g of 1,4-butanediol, 1.0 g of propylene glycol, and 4.0 g of pure water, and then the resultant mixture was heat-treated at 210° C. for 25 minutes. Furthermore, the resultant particles were disintegrated to such a degree that they could pass through a JIS standard sieve having a mesh opening size of 600 μm. As a result, surface-crosslink-treated water-absorbent resin particles (C1-2A10) were obtained. The water-absorbent resin particles (C1-2A10) displayed a CRC of 28.0 g/g, an SFC of 60 ($10^{-7} \cdot cm^3 \cdot s \cdot g^{-1}$), and a CSF of 24.0 g/g.

Next, 100 mass parts of the water-absorbent resin particles (C1-2A10) were uniformly mixed with 0.3 mass part of Reolosil QS-20 (hydrophilic amorphous silica produced by Tokuyama Corporation), thus obtaining a water-absorbing agent (D1-2A10). The resultant water-absorbing agent (D1-2A10) was also of the shape of a powder. The results of having measured its properties are shown in Tables 1, 2 and 3.

Example 3

An amount of 100 g of the water-absorbent resin particles (B1A10) as obtained from Example 1 were mixed with a surface-treating agent comprising a mixed liquid of 2.0 g of propylene glycol and 4.0 g of pure water, and then the resultant mixture was heat-treated at 215° C. for 30 minutes. Furthermore, the resultant particles were disintegrated to such a degree that they could pass through a JIS standard sieve having a mesh opening size of 600 μm. As a result, surface-crosslink-treated water-absorbent resin particles (C1-3A10) were obtained. The water-absorbent resin particles (C1-

3A10) displayed a CRC of 27.5 g/g, an SFC of 66 ($10^{-7}\cdot cm^3\cdot s\cdot g^{-1}$), and a CSF of 23.8 g/g.

Next, 100 mass parts of the water-absorbent resin particles (C1-3A10) were uniformly mixed with 0.3 mass part of Reolosil QS-20 (hydrophilic amorphous silica produced by Tokuyama Corporation), thus obtaining a water-absorbing agent (D1-3A10). The resultant water-absorbing agent (D1-3A10) was also of the shape of a powder. The results of having measured its properties are shown in Tables 1, 2 and 3.

Example 4

(1) Polymerization

In a reactor as prepared by lidding a jacketed stainless twin-arm kneader of 10 liters in capacity having two sigma-type blades, there was prepared a reaction liquid by dissolving 11.7 g (0.10 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer (4) was taken out after 30 minutes from the start of the polymerization.

The crosslinked hydrogel polymer (4) as obtained above was in the form of finely divided pieces having diameters of not larger than about 5 mm. This finely divided crosslinked hydrogel polymer (4) was spread onto a metal gauze of 50 meshes (mesh opening size: 300 μm) and then hot-air-dried at 180° C. for 50 minutes, thus obtaining a water-absorbent resin (A4) which was of the irregular shape and easy to pulverize, such as in the form of particles, a powder, or a particulate dried material agglomerate.

(2) Pulverization and Classification

The resultant water-absorbent resin (A4) was pulverized with a roll mill and then further classified with a JIS standard sieve having a mesh opening size of 600 μm. Next, particles having passed through the 600 μm in the aforementioned operation were classified with a JIS standard sieve having a mesh opening size of 180 μm, whereby water-absorbent resin particles (B4F) passing through the JIS standard sieve having the mesh opening size of 180 μm were removed, thus obtaining water-absorbent resin particles (B4).

(3) Agglomeration of Fine Powder

The water-absorbent resin particles (B4F) having been removed in the above "(2) Pulverization and classification" were agglomerated in the same way as of Example 1-(3). The resultant agglomerated material was pulverized and classified by the same procedure as of the aforementioned Example 1-(2), thus obtaining agglomerated water-absorbent resin particles (B4A).

(4) Mixing of Fine-Powder-Agglomerated Product

An amount of 90 mass parts of the water-absorbent resin particles (B4) and 10 mass parts of the water-absorbent resin particles (B4A) were uniformly mixed together to obtain water-absorbent resin particles (B4A10). The CRC of the water-absorbent resin particles (B4A10) was 31.8 g/g.

(5) Surface Treatment

An amount of 100 g of the water-absorbent resin particles (B4A10) as obtained from the aforementioned step were mixed with a surface-treating agent comprising a mixed liquid of 0.3 g of 1,4-butanediol, 1.5 g of propylene glycol, and 3.0 g of pure water, and then the resultant mixture was heat-treated at 220° C. for 25 minutes. Furthermore, the resultant particles were disintegrated to such a degree that they could pass through a JIS standard sieve having a mesh opening size of 600 μm. As a result, surface-crosslink-treated water-absorbent resin particles (C4-4A10) were obtained. The water-absorbent resin particles (C4-4A10) displayed a CRC of 27.0 g/g, an SFC of 70 ($10^{-7}\cdot cm^3\cdot s\cdot g^{-1}$), and a CSF of 23.1 g/g.

Next, 100 mass parts of the water-absorbent resin particles (C4-4A10) were uniformly mixed with 0.3 mass part of Reolosil QS-20 (hydrophilic amorphous silica produced by Tokuyama Corporation), thus obtaining a water-absorbing agent (D4-4A10). The resultant water-absorbing agent (D4-4A10) was also of the shape of a powder. The results of having measured its properties are shown in Tables 1, 2 and 3.

Example 5

An amount of 100 g of the water-absorbent resin particles (B4A10) as obtained from Example 4 were mixed with a surface-treating agent comprising a mixed liquid of 0.4 g of 1,4-butanediol, 0.6 g of propylene glycol, and 3.0 g of pure water, and then the resultant mixture was heat-treated at 210° C. for 30 minutes. Furthermore, the resultant particles were disintegrated to such a degree that they could pass through a JIS standard sieve having a mesh opening size of 600 μm. As a result, surface-crosslink-treated water-absorbent resin particles (C4-5A10) were obtained. The water-absorbent resin particles (C4-5A10) displayed a CRC of 26.0 g/g, an SFC of 78 ($10^{-7}\cdot cm^3\cdot s\cdot g^{-1}$), and a CSF of 22.1 g/g.

Next, 100 mass parts of the water-absorbent resin particles (C4-5A10) were uniformly mixed with 0.3 mass part of Reolosil QS-20 (hydrophilic amorphous silica produced by Tokuyama Corporation), thus obtaining a water-absorbing agent (D4-5A10). The resultant water-absorbing agent (D4-5A10) was also of the shape of a powder. The results of having measured its properties are shown in Tables 1, 2 and 3.

Example 6

An amount of 100 mass parts of the water-absorbent resin particles (C4-5A10), as obtained from Example 5, were uniformly mixed with 0.2 mass part of Reolosil QS-20 (hydrophilic amorphous silica produced by Tokuyama Corporation), thus obtaining a water-absorbing agent (D4-6A10). The resultant water-absorbing agent (D4-6A10) was also of the shape of a powder. The results of having measured its properties are shown in Tables 1, 2 and 3.

Example 7

(1) Polymerization

The water-absorbent resin (A4) was obtained in the same way as of Example 4.

(2) Pulverization and Classification

The resultant water-absorbent resin (A4) was pulverized with a roll mill and then further classified with a JIS standard sieve having a mesh opening size of 600 µm. Next, particles having passed through the 600 µm in the aforementioned operation were classified with a JIS standard sieve having a mesh opening size of 150 µm, whereby water-absorbent resin particles (B7F) passing through the JIS standard sieve having the mesh opening size of 150 µm were removed, thus obtaining water-absorbent resin particles (B7).

(3) Agglomeration of Fine Powder

The water-absorbent resin particles (B7F) having been removed in the above "(2) Pulverization and classification" were agglomerated in the same way as of Example 1-(3). The resultant agglomerated material was pulverized and classified by the same procedure as of the aforementioned (2), thus obtaining agglomerated water-absorbent resin particles (B7A).

(4) Mixing of Fine-Powder-Agglomerated Product

An amount of 90 mass parts of the water-absorbent resin particles (B7) and 10 mass parts of the water-absorbent resin particles (B7A) were uniformly mixed together to obtain water-absorbent resin particles (B7A10). Similarly, 80 mass parts of the water-absorbent resin particles (B7) and 20 mass parts of the water-absorbent resin particles (B7A) were uniformly mixed together to obtain water-absorbent resin particles (B7A20). Similarly, 70 mass parts of the water-absorbent resin particles (B7) and 30 mass parts of the water-absorbent resin particles (B7A) were uniformly mixed together to obtain water-absorbent resin particles (B7A30). The CRC of the water-absorbent resin particles (B7) was 32.1 g/g, the CRC of the water-absorbent resin particles (B7A10) was 31.8 g/g, the CRC of the water-absorbent resin particles (B7A20) was 31.6 g/g, and the CRC of the water-absorbent resin particles (B7A30) was 31.3 g/g.

(5) Surface Treatment

An amount of 100 g of the water-absorbent resin particles (B7) as obtained from the aforementioned step were mixed with a surface-treating agent comprising a mixed liquid of 0.5 g of ethylene carbonate and 4.5 g of pure water, and then the resultant mixture was heat-treated at 200° C. for 30 minutes. Furthermore, the resultant particles were disintegrated to such a degree that they could pass through a JIS standard sieve having a mesh opening size of 600 µm. As a result, surface-crosslink-treated water-absorbent resin particles were obtained. Next, 100 mass parts of these water-absorbent resin particles were uniformly mixed with 1.0 mass part of Sipernat 22S (hydrophilic amorphous silica obtained from DEGUSSA Corporation), thus obtaining a water-absorbing agent (D7-7A00). The resultant water-absorbing agent (D7-7A00) was also of the shape of a powder. The results of having measured its properties are shown in Tables 1, 2 and 3.

A water-absorbing agent (D7-7A10) was obtained in the same way as the above except that the water-absorbent resin particles (B7) were replaced with the water-absorbent resin particles (B7A10). The resultant water-absorbing agent (D7-7A10) was also of the shape of a powder. The results of having measured its properties are shown in Tables 1, 2 and 3.

A water-absorbing agent (D7-7A20) was obtained in the same way as the above except that the water-absorbent resin particles (B7) were replaced with the water-absorbent resin particles (B7A20). The resultant water-absorbing agent (D7-7A20) was also of the shape of a powder. The results of having measured its properties are shown in Tables 1, 2 and 3.

A water-absorbing agent (D7-7A30) was obtained in the same way as the above except that the water-absorbent resin particles (B7) were replaced with the water-absorbent resin particles (B7A30). The resultant water-absorbing agent (D7-7A30) was also of the shape of a powder. The results of having measured its properties are shown in Tables 1, 2 and 3.

Example 8

An amount of 100 mass parts of the water-absorbent resin particles (C4-5A10) and 0.5 mass part of aluminum sulfate tetradeca- to octadecahydrates (as prepared by a method in which those which had been obtained from Wako Pure Chemical Industries, Ltd. were finely pulverized by grinding them down with a mortar) were uniformly mixed together, thus obtaining a water-absorbing agent (D4-8A10). The resultant water-absorbing agent (D4-8A10) was also of the shape of a powder. The results of having measured its properties are shown in Tables 1, 2 and 3.

Example 9

An amount of 100 mass parts of the water-absorbent resin particles (C4-5A10) and 0.5 mass part of poly(aluminum chloride) (obtained from Kishida Kagaku K.K.) were uniformly mixed together, thus obtaining a water-absorbing agent (D4-9A10). The resultant water-absorbing agent (D4-9A10) was also of the shape of a powder. The results of having measured its properties are shown in Tables 1, 2 and 3.

Example 10

The same operation as of Example 4 was carried out except that the conditions of the roll mill were adjusted so that the particle diameters of the resultant water-absorbent resin particles could be still finer ones. Thereby, surface-crosslink-treated water-absorbent resin particles (C4-10A10) were obtained. An amount of 100 mass parts of the water-absorbent resin particles (C4-10A10) and 0.5 mass part of Laponite RD (obtained from Nippon Silica Kogyo K.K.) were uniformly mixed together, thus obtaining a water-absorbing agent (D4-10A10). The resultant water-absorbing agent (D4-10A10) was also of the shape of a powder. The results of having measured its properties are shown in Tables 1, 2 and 3.

Example 11

The same operation as of Example 10 was carried out except that the conditions of the roll mill were adjusted so that the particle diameters of the resultant water-absorbent resin particles could be still finer ones. Thereby, surface-crosslink-treated water-absorbent resin particles (C4-11A10) were obtained. An amount of 100 mass parts of the water-absorbent resin particles (C4-11A10) and 0.5 mass part of Kyowaad 700 (obtained from Kyowa Kagaku Kogyo K.K.) were uniformly mixed together, thus obtaining a water-absorbing agent (D4-11A10). The resultant water-absorbing agent (D4-11A10) was also of the shape of a powder. The results of having measured its properties are shown in Tables 1, 2 and 3.

Example 12

The same operation as of Example 11 was carried out except that the conditions of the roll mill were adjusted so that the particle diameters of the resultant water-absorbent resin particles could be still finer ones. Thereby, surface-crosslink-treated water-absorbent resin particles (C4-12A10) were obtained. An amount of 100 mass parts of the water-absorbent resin particles (C4-12A10) and 0.7 mass part of alumina (0.5 μm, obtained from Kanto Chemical Co., Inc.) were uniformly mixed together, thus obtaining a water-absorbing agent (D4-12A10). The resultant water-absorbing agent (D4-12A10) was also of the shape of a powder. The results of having measured its properties are shown in Tables 1, 2 and 3.

Example 13

A glass container of 6 cm in diameter and 11 cm in height was charged with 30 g of the water-absorbing agent (D4-5A10) and 10 g of glass beads of 6 mm in diameter, and then attached to a paint shaker (product No. 488 of Toyo Seiki Seisakusho K.K.), and then shaken at 800 cycles/min (CPM) for 10 minutes. Thereafter, the glass beads were removed, thus obtaining a water-absorbing agent (D4-13A10D). The resultant water-absorbing agent (D4-13A10D) was also of the shape of a powder. The results of having measured its properties are shown in Tables 1, 2 and 3.

Example 14

A water-absorbing agent (D7-14A10D) was obtained in the same way as of Example 13 except that the water-absorbing agent (D7-7A10) was substituted. The resultant water-absorbing agent (D7-14A10D) was also of the shape of a powder. The results of having measured its properties are shown in Tables 1, 2 and 3.

Example 15

(1) Polymerization

The water-absorbent resin (A4) was obtained in the same way as of Example 4.

(2) Pulverization and Classification

The resultant water-absorbent resin (A4) was pulverized with a roll mill and then further classified with a JIS standard sieve having a mesh opening size of 500 μm. Next, particles having passed through the 500 μm in the aforementioned operation were classified with a JIS standard sieve having a mesh opening size of 150 μm, whereby water-absorbent resin particles (B15F) passing through the JIS standard sieve having the mesh opening size of 150 μm were removed, thus obtaining water-absorbent resin particles (B15).

(3) Agglomeration of Fine Powder

The water-absorbent resin particles (B15F) having been removed in the above "(2) Pulverization and classification" were agglomerated in the same way as of Example 1-(3). The resultant agglomerated material was pulverized and classified by the same procedure as of the aforementioned (2), thus obtaining agglomerated water-absorbent resin particles (B15A).

(4) Mixing of Fine-Powder-Agglomerated Product

An amount of 90 mass parts of the water-absorbent resin particles (B15) and 10 mass parts of the water-absorbent resin particles (B15A) were uniformly mixed together to obtain water-absorbent resin particles (B15A10). The CRC of the water-absorbent resin particles (B15A10) was 31.7 g/g.

(5) Surface Treatment

An amount of 100 g of the water-absorbent resin particles (B15A10) as obtained from the aforementioned step were mixed with a surface-treating agent comprising a mixed liquid of 0.4 g of 2-oxazolidinone, 2.0 g of propylene glycol, and 4.0 g of pure water, and then the resultant mixture was heat-treated at 185° C. for 30 minutes. Furthermore, the resultant particles were disintegrated to such a degree that they could pass through a JIS standard sieve having a mesh opening size of 500 μm. As a result, surface-crosslink-treated water-absorbent resin particles (C15-15A10) were obtained. The water-absorbent resin particles (C15-15A10) displayed a CRC of 26.0 g/g, an SFC of 39 ($10^{-7} \cdot cm^3 \cdot s \cdot g^{-1}$), and a CSF of 23.9 g/g.

Next, 100 mass parts of the water-absorbent resin particles (C15-15A10) were uniformly mixed with 1.0 g of magnesium oxide (0.2 μm, obtained from Wako Pure Chemical Industries, Ltd.), thus obtaining a water-absorbing agent (D15-15A10). The resultant water-absorbing agent (D15-15A10) was also of the shape of a powder. The results of having measured its properties are shown in Tables 1, 2 and 3.

Example 16

The same operation as of Example 4-(1) to (4) was carried out except that the conditions of the roll mill were adjusted so that the particle diameters of the resultant water-absorbent resin particles could be still coarser ones. Thereby, water-absorbent resin particles (B16A10) were obtained. An amount of 100 g of the water-absorbent resin particles (B16A10) were mixed with a surface-treating agent comprising a mixed liquid of 1.0 g of ethylene carbonate and 4.0 g of pure water, and then the resultant mixture was heat-treated at 200° C. for 40 minutes. Furthermore, the resultant particles were disintegrated to such a degree that they could pass through a JIS standard sieve having a mesh opening size of 600 μm. As a result, surface-crosslink-treated water-absorbent resin particles (C16-16A10) were obtained. The water-absorbent resin particles (C16-16A10) displayed a CRC of 23.1 g/g, an SFC of 113 ($10^{-7} \cdot cm^3 \cdot s \cdot g^{-1}$), and a CSF of 19.2 g/g.

Next, 100 mass parts of the water-absorbent resin particles (C16-16A10) were uniformly mixed with 1.0 g of bentonite (obtained from Kanto Chemical Co., Inc.), thus obtaining a water-absorbing agent (D16-16A10). The resultant water-absorbing agent (D16-16A10) was also of the shape of a powder. The results of having measured its properties are shown in Tables 1, 2 and 3.

Example 17

An amount of 100 mass parts of the water-absorbent resin particles (C16-16A10) and 2.0 mass parts of talc (obtained from Kanto Chemical Co., Inc.) were uniformly mixed together, thus obtaining a water-absorbing agent (D16-17A10). The resultant water-absorbing agent (D16-17A10) was also of the shape of a powder. The results of having measured its properties are shown in Tables 1, 2 and 3.

Example 18

An amount of 100 mass parts of the water-absorbent resin particles (C16-16A10) and 1.0 mass part of glass powder Nisshinbo PFE-301s (obtained from Nisshinbo) were uniformly mixed together, thus obtaining a water-absorbing agent (D16-18A10). The resultant water-absorbing agent (D16-18A10) was also of the shape of a powder. The results of having measured its properties are shown in Tables 1, 2 and 3.

Example 19

An amount of 100 mass parts of the water-absorbent resin particles (C15-15A10) and 1.5 mass parts of Sipernat 2200 (obtained from DEGUSSA Corporation) were uniformly mixed together, thus obtaining a water-absorbing agent (D15-19A10). The resultant water-absorbing agent (D15-19A10) was also of the shape of a powder. The results of having measured its properties are shown in Tables 1, 2 and 3.

Example 20

An amount of 100 mass parts of the water-absorbent resin particles (C15-15A10) and 0.7 mass part of fuller's earth (obtained from Kanto Chemical Co., Inc.) were uniformly mixed together, thus obtaining a water-absorbing agent (D15-20A10). The resultant water-absorbing agent (D15-20A10) was also of the shape of a powder. The results of having measured its properties are shown in Tables 1, 2 and 3.

Example 21

An amount of 100 mass parts of the water-absorbent resin particles (C15-15A10) and 1.0 mass part of kaolin (obtained from Kanto Chemical Co., Inc.) were uniformly mixed together, thus obtaining a water-absorbing agent (D15-21A10). The resultant water-absorbing agent (D15-21A10) was also of the shape of a powder. The results of having measured its properties are shown in Tables 1, 2 and 3.

Example 22

An amount of 100 mass parts of the water-absorbent resin particles (C4-5A10), 0.1 mass part of Reolosil QS-20 (hydrophilic amorphous silica produced by Tokuyama Corporation), and 0.5 mass part of aluminum sulfate tetradeca- to octadecahydrates (as prepared by a method in which those which had been obtained from Wako Pure Chemical Industries, Ltd. were finely pulverized by grinding them down with a mortar) were uniformly mixed together, thus obtaining a water-absorbing agent (D4-22A10). The resultant water-absorbing agent (D4-22A10) was also of the shape of a powder. The results of having measured its properties are shown in Tables 1, 2 and 3.

Example 23

(1) Polymerization

In a jacketed stainless reactor of 10 liters in capacity as equipped with stirring blades, there was prepared a reaction liquid by dissolving 9.36 g (0.08 mol %) of polyethylene glycol diacrylate into 5,438 g of aqueous solution of sodium acrylate having a neutralization degree of 71.3 mol % (monomer concentration: 39 mass %). Next, this reaction liquid was deaerated under an atmosphere of nitrogen gas for 30 minutes. Subsequently, 54.5 g of 10 mass % aqueous solution of 2,2'-azobis(2-methylpropionamidine)dihydrochloride as a foaming agent precursor was added to the aqueous monomer solution under stirred conditions. Thereafter, the resultant aqueous solution was stirred at a temperature of 25° C. under a nitrogen gas flow. After about 7 minutes from the start of the stirring, the aqueous solution became white turbid to form a white fine particulate solid having an average particle diameter of 9 μm. This fine particulate solid was 2,2'-azobis(2-methylpropionamidine)diacrylate as a foaming agent. This 2,2'-azobis(2-methylpropionamidine)diacrylate was in a state dispersed uniformly in the aqueous monomer solution. At that time (after 10 minutes from the start of the stirring), 29.34 g of 10 mass % aqueous sodium persulfate solution and 24.45 g of 0.1 mass % aqueous L-ascorbic acid solution were added to the aqueous monomer solution while it was stirred. After having been stirred enough, the aqueous monomer solution was left stationary. As a result, polymerization started after about 1 minute. Thereby a bubble-containing hydrogel was obtained after 20 minutes. Then, the formed gel was pulverized and then spread onto a metal gauze of 50 meshes (mesh opening size: 300 μm) and then hot-air-dried at 180° C. for 50 minutes, thus obtaining a water-absorbent resin (A23) which was of the irregular shape and had a porous structure due to bubbles and was easy to pulverize, such as in the form of particles, a powder, or a particulate dried material agglomerate.

(2) Pulverization and Classification

The resultant water-absorbent resin (A23) was pulverized with a roll mill and then further classified with a JIS standard sieve having a mesh opening size of 600 μm. Next, particles having passed through the 600 μm in the aforementioned operation were classified with a JIS standard sieve having a mesh opening size of 180 μm, whereby water-absorbent resin particles (B23F) passing through the JIS standard sieve having the mesh opening size of 180 μm were removed, thus obtaining water-absorbent resin particles (B23).

(3) Mixing

An amount of 90 mass parts of the water-absorbent resin particles (B1) and 10 mass parts of the water-absorbent resin particles (B23) were uniformly mixed together to obtain water-absorbent resin particles (B23F10). The CRC of the water-absorbent resin particles (B23F10) was 33.6 g/g.

(4) Surface Treatment

An amount of 100 g of the water-absorbent resin particles (B23F10) as obtained from the aforementioned step were mixed with a surface-treating agent comprising a mixed liquid of 1.0 g of 1,4-butanediol, 2.0 g of propylene glycol, and 3.0 g of pure water, and then the resultant mixture was heat-treated at 195° C. for 30 minutes. Furthermore, the resultant particles were disintegrated to such a degree that they could pass through a JIS standard sieve having a mesh opening size of 600 μm. As a result, surface-crosslink-treated water-absorbent resin particles (C23-23F10) were obtained. The water-absorbent resin particles (C23-23F10) displayed a CRC of 26.3 g/g, an SFC of 70 ($10^{-7} \cdot cm^3 \cdot s \cdot g^{-1}$), and a CSF of 21.7 g/g.

Next, 100 mass parts of the water-absorbent resin particles (C23-23F10) were uniformly mixed with 0.3 mass part of Reolosil QS-20 (hydrophilic amorphous silica produced by Tokuyama Corporation), thus obtaining a water-absorbing agent (D23-23F10). The resultant water-absorbing agent (D23-23F10) was also of the shape of a powder. The results of having measured its properties are shown in Tables 1, 2 and 3.

Example 24

An amount of 100 mass parts of the water-absorbent resin particles (C16-16A10) and 1.0 mass part of fine particles of polyethylene were uniformly mixed together, thus obtaining a water-absorbing agent (D16-24A10). The resultant water-absorbing agent (D16-24A10) was also of the shape of a powder. The results of having measured its properties are shown in Tables 1, 2 and 3.

Example 25

An amount of 100 mass parts of the water-absorbent resin particles (C15-15A10) and 1.0 mass part of Sipernat D17 (obtained from DEGUSSA Corporation) were uniformly mixed together, thus obtaining a water-absorbing agent (D15-25A10). The resultant water-absorbing agent (D15-25A10) was also of the shape of a powder. The results of having measured its properties are shown in Tables 1, 2 and 3.

Example 26

An amount of 100 mass parts of the water-absorbent resin particles (C16-16A10) and 0.3 mass part of Aerosil R-972 (hydrophobic amorphous silica obtained from DEGUSSA Corporation) were uniformly mixed together, thus obtaining a water-absorbing agent (D16-26A10). The resultant water-absorbing agent (D16-26A10) was also of the shape of a powder. The results of having measured its properties are shown in Tables 1, 2 and 3.

Example 27

An amount of 100 mass parts of the water-absorbent resin particles (C4-5A10) and 1.5 mass parts of polyethyleneimine P-1000 (produced by Nippon Shokubai Co., Ltd.) were uniformly mixed together, and then the resultant mixture was dried at 90° C. for 60 minutes. Next, the dried mixture was passed through a sieve having a mesh opening size of 600 µm, thus obtaining a water-absorbing agent (D4-27A10). The resultant water-absorbing agent (D4-27A10) was also of the shape of a powder. The results of having measured its properties are shown in Tables 1, 2 and 3.

Example 28

An amount of 100 mass parts of the water-absorbent resin particles (C15-15A10) and 3 mass parts of Catiofast PR8106 (produced by BASF) were uniformly mixed together, and then the resultant mixture was dried at 90° C. for 60 minutes. Next, the dried mixture was passed through a sieve having a mesh opening size of 500 µm, thus obtaining a water-absorbing agent (D15-28A10). The resultant water-absorbing agent (D15-28A10) was also of the shape of a powder. The results of having measured its properties are shown in Tables 1, 2 and 3.

Example 29

An amount of 100 mass parts of the water-absorbent resin particles (C16-16A10) and 2 mass parts of 10 mass % aqueous solution of polyamidine (produced by Mitsubishi Chemical Corporation) were uniformly mixed together, and then the resultant mixture was dried at 90° C. for 60 minutes. Next, the dried mixture was passed through a sieve having a mesh opening size of 600 µm, thus obtaining a water-absorbing agent (D16-29A10). The resultant water-absorbing agent (D16-29A10) was also of the shape of a powder. The results of having measured its properties are shown in Tables 1, 2 and 3.

Comparative Example 1

(1) Polymerization

The water-absorbent resin (A4) was obtained in the same way as of Example 4.

(2) Pulverization and Classification

The resultant water-absorbent resin (A4) was pulverized with a roll mill and then further classified with a JIS standard sieve having a mesh opening size of 850 µm, thus obtaining a water-absorbent resin, most of which was in the range of not larger than 850 µm. Next, this water-absorbent resin was classified with a JIS standard sieve having a mesh opening size of 150 µm, whereby water-absorbent resin particles (X1F) passing through the JIS standard sieve having the mesh opening size of 150 µm were removed, thus obtaining water-absorbent resin particles (X1).

(3) Surface Treatment

An amount of 100 g of the water-absorbent resin particles (X1) as obtained from the aforementioned step were mixed with a surface-treating agent comprising a mixed liquid of 0.4 g of 1,4-butanediol, 0.6 g of propylene glycol, and 3.0 g of pure water, and then the resultant mixture was heat-treated at 212° C. for 30 minutes. Furthermore, the resultant particles were disintegrated to such a degree that they could pass through a JIS standard sieve having a mesh opening size of 850 µm. As a result, surface-crosslink-treated water-absorbent resin particles (X1-1A00) were obtained. The water-absorbent resin particles (X1-1A00) displayed a CRC of 26.5 g/g, an SFC of 98 ($10^{-7} \cdot cm^3 \cdot s \cdot g^{-1}$), and a CSF of 19.1 g/g.

Next, 100 mass parts of the water-absorbent resin particles (X1-1A00) were uniformly mixed with 0.3 mass part of Reolosil QS-20 (hydrophilic amorphous silica produced by Tokuyama Corporation), thus obtaining a comparative water-absorbing agent (Y1-1A00). The resultant comparative water-absorbing agent (Y1-1A00) was also of the shape of a powder. The results of having measured its properties are shown in Tables 1, 2 and 3.

Comparative Example 2

An amount of 100 mass parts of the water-absorbent resin particles (X1-1A00), as obtained from Comparative Example 1, and 0.2 mass part of Reolosil QS-20 (hydrophilic amorphous silica produced by Tokuyama Corporation) were uniformly mixed together, thus obtaining a comparative water-absorbing agent (Y1-2A00), The resultant comparative water-absorbing agent (Y1-2A00) was also of the shape of a powder. The results of having measured its properties are shown in Tables 1, 2 and 3.

Comparative Example 3

An amount of 100 mass parts of the water-absorbent resin particles (X1-1A00), as obtained from Comparative Example 1, and 0.5 mass part of poly(aluminum chloride) (obtained from Kishida Kagaku K.K.) were uniformly mixed together, thus obtaining a comparative water-absorbing agent (Y1-3A00). The resultant comparative water-absorbing agent (Y1-3A00) was also of the shape of a powder. The results of having measured its properties are shown in Tables 1, 2 and 3.

Comparative Example 4

An amount of 100 mass parts of the water-absorbent resin particles (X1-1A00), as obtained from Comparative Example 1, and 1.0 mass part of kaolin (obtained from Kanto Chemical Co., Inc.) were uniformly mixed together, thus obtaining a comparative water-absorbing agent (Y1-4A00). The resultant comparative water-absorbing agent (Y1-4A00) was also of the shape of a powder. The results of having measured its properties are shown in Tables 1, 2 and 3.

Comparative Example 5

An amount of 0.5 mass part of aluminum sulfate tetradecato octadecahydrates (as prepared by a method in which those which had been obtained from Wako Pure Chemical Industries, Ltd. were finely pulverized by grinding them down with a mortar) and 4.5 mass parts of pure water were mixed together to prepare an aqueous solution, and then this aqueous solution was uniformly mixed with 100 mass parts of the water-absorbing agent (C4-5A10), and then the resultant mixture was dried at 60° C. for 20 minutes and then passed through a JIS standard sieve having a mesh opening size of 850 µm, thus obtaining a comparative water-absorbing agent (Y5-5A00). The resultant comparative water-absorbing agent (Y5-5A00) was also of the shape of a powder. The results of having measured its properties are shown in Tables 1, 2 and 3.

Comparative Example 6

(1) Polymerization

In a reactor as prepared by lidding a jacketed stainless twin-arm kneader of 10 liters in capacity having two sigma-type blades, there was prepared a reaction liquid by dissolving 3.82 g (0.033 mol %) of polyethylene glycol diacrylate into 5,443 g of aqueous solution of sodium acrylate having a neutralization degree of 75 mol % (monomer concentration: 39 mass %). Next, this reaction liquid was deaerated under an atmosphere of nitrogen gas for 30 minutes. Subsequently, 29.27 g of 10 mass % aqueous sodium persulfate solution and 24.22 g of 0.1 mass % aqueous L-ascorbic acid solution were added thereto under stirred conditions. As a result, polymerization started after about 1 minute. Then, the polymerization was carried out in the range of 20 to 95° C. while the forming gel was pulverized. Then, the resultant crosslinked hydrogel polymer (c6) was taken out after 30 minutes from the start of the polymerization.

The crosslinked hydrogel polymer (c6) as obtained above was in the form of finely divided pieces having diameters of not larger than about 5 mm. This finely divided crosslinked hydrogel polymer (c6) was spread onto a metal gauze of 50 meshes (mesh opening size: 300 µm) and then hot-air-dried at 180° C. for 50 minutes, thus obtaining a water-absorbent resin (V6) which was of the irregular shape and easy to pulverize, such as in the form of particles, a powder, or a particulate dried material agglomerate.

(2) Pulverization and Classification

The resultant water-absorbent resin (V6) was pulverized with a roll mill and then further classified with a JIS standard sieve having a mesh opening size of 600 µm. Next, particles having passed through the 600 µm in the aforementioned operation were classified with a JIS standard sieve having a mesh opening size of 150 µm, whereby water-absorbent resin particles (W6F) passing through the JIS standard sieve having the mesh opening size of 150 µm were removed, thus obtaining water-absorbent resin particles (W6).

(3) Surface Treatment

An amount of 100 g of the water-absorbent resin particles (W6) as obtained from the aforementioned step were mixed with a surface-treating agent comprising a mixed liquid of 0.1 g of ethylene glycol diglycidyl ether, 1.0 g of propylene glycol, and 3.0 g of pure water, and then the resultant mixture was heat-treated at 195° C. for 30 minutes. Furthermore, the resultant particles were disintegrated to such a degree that they could pass through a JIS standard sieve having a mesh opening size of 600 µm. As a result, surface-crosslink-treated water-absorbent resin particles (X6-6A00) were obtained. The water-absorbent resin particles (X6-6A00) displayed a CRC of 35.2 g/g, an SFC of 2 ($10^{-7} \cdot cm^3 \cdot s \cdot g^{-1}$), and a CSF of 28.2 g/g.

Next, 100 mass parts of the water-absorbent resin particles (X6-6A00) were uniformly mixed with 0.3 mass part of Reolosil QS-20 (hydrophilic amorphous silica produced by Tokuyama Corporation), thus obtaining a comparative water-absorbing agent (Y6-6A00). The resultant comparative water-absorbing agent (Y6-6A00) was also of the shape of a powder. The results of having measured its properties are shown in Tables 1, 2 and 3.

TABLE 1

| Water-absorbing agent | CRC g/g | AAP g/g | SFC $10^{-7} \cdot cm^3 \cdot s \cdot g^{-1}$ | CSF g/g | 260-8* CSF | Water content mass % | D50 µm | σζ |
|---|---|---|---|---|---|---|---|---|
| D1-1A10 | 28.5 | 21.2 | 85 | 23.2 | 74 | 9.8 | 315 | 0.37 |
| D1-2A10 | 28.0 | 21.5 | 106 | 22.1 | 83 | 8.9 | 315 | 0.37 |
| D1-3A10 | 27.5 | 21.9 | 128 | 21.1 | 91 | 8.1 | 314 | 0.37 |
| D4-4A10 | 27.0 | 21.5 | 160 | 17.8 | 118 | 8.3 | 316 | 0.37 |
| D4-5A10 | 26.0 | 21.3 | 178 | 15.1 | 139 | 7.9 | 314 | 0.36 |
| D4-6A10 | 26.4 | 22.3 | 136 | 20.9 | 93 | 7.7 | 315 | 0.36 |
| D7-7A00 | 26.4 | 21.9 | 138 | 20.7 | 94 | 7.6 | 303 | 0.38 |
| D7-7A10 | 26.2 | 22 | 137 | 21.3 | 90 | 7.8 | 302 | 0.38 |
| D7-7A20 | 26.2 | 22 | 140 | 21.8 | 86 | 7.7 | 298 | 0.38 |
| D7-7A30 | 26.1 | 22.1 | 138 | 22.5 | 80 | 7.7 | 297 | 0.38 |

TABLE 1-continued

| | CRC g/g | AAP g/g | SFC $10^{-7} \cdot cm^3 \cdot s \cdot g^{-1}$ | CSF g/g | 260-8* CSF | Water content mass % | D50 μm | σζ |
|---|---|---|---|---|---|---|---|---|
| D4-8A10 | 25.9 | 23.7 | 150 | 20.4 | 97 | 7.9 | 315 | 0.36 |
| D4-9A10 | 26 | 23.7 | 137 | 18.3 | 114 | 7.8 | 314 | 0.36 |
| D4-10A10 | 26 | 22 | 135 | 21.5 | 88 | 7.6 | 297 | 0.34 |
| D4-11A10 | 25.8 | 23.1 | 132 | 22.1 | 83 | 7.5 | 280 | 0.35 |
| D4-12A10 | 26.1 | 22.4 | 131 | 22.9 | 77 | 7.7 | 265 | 0.34 |
| D4-13A10D | 26.1 | 22.5 | 136 | 20.4 | 97 | 7.6 | 306 | 0.37 |
| D7-14A10D | 26.3 | 23.3 | 123 | 22.3 | 82 | 7.5 | 294 | 0.37 |
| D15-15A10 | 25.8 | 22.2 | 90 | 21.4 | 88.8 | 7.8 | 324 | 0.30 |
| D16-16A10 | 22.8 | 20.1 | 126 | 18.7 | 110 | 7.7 | 340 | 0.37 |
| D16-17A10 | 22.3 | 20 | 124 | 18.6 | 111 | 7.3 | 337 | 0.38 |
| D16-18A10 | 23.1 | 20.2 | 128 | 18.3 | 114 | 7.4 | 336 | 0.38 |
| D15-19A10 | 25.8 | 21.2 | 92 | 21.1 | 91 | 7.8 | 324 | 0.30 |
| D15-20A10 | 25.9 | 23.2 | 75 | 23.6 | 71 | 7.8 | 320 | 0.32 |
| D15-21A10 | 25.9 | 23.5 | 73 | 23.7 | 70 | 7.7 | 328 | 0.29 |
| D4-22A10 | 25.9 | 23.1 | 161 | 20 | 100 | 7.6 | 314 | 0.37 |
| D23-23F10 | 26.1 | 20.1 | 153 | 15 | 140 | 7.8 | 315 | 0.37 |
| D16-24A10 | 23 | 20.3 | 134 | 11.2 | 170 | 7.4 | 348 | 0.38 |
| D15-25A10 | 25.9 | 21.1 | 134 | 10.9 | 173 | 7.7 | 322 | 0.31 |
| D16-26A10 | 22.5 | 20 | 178 | 9.8 | 182 | 7.3 | 341 | 0.38 |
| D4-27A10 | 25.9 | 21.5 | 157 | 6.5 | 208 | 7.7 | 356 | 0.33 |
| D15-28A10 | 25.6 | 21.4 | 119 | 7.8 | 198 | 7.7 | 334 | 0.29 |
| D16-29A10 | 25.8 | 21.1 | 135 | 6.2 | 210 | 7.6 | 342 | 0.38 |
| Comparative water-absorbing agent | | | | | | | | |
| Y1-1A00 | 26.4 | 21.3 | 183 | 7.6 | 199 | 7.9 | 441 | 0.49 |
| Y1-2A00 | 26.4 | 21.9 | 133 | 8.9 | 189 | 7.8 | 437 | 0.51 |
| Y1-3A00 | 26.2 | 21.5 | 151 | 10.1 | 179 | 7.6 | 431 | 0.49 |
| Y1-4A00 | 26.3 | 22.3 | 119 | 14.9 | 141 | 7.7 | 429 | 0.51 |
| Y5-5A00 | 25.8 | 21.3 | 160 | 9.8 | 182 | 7.7 | 432 | 0.50 |
| Y6-6A00 | 35.2 | 19.7 | 10 | 22.1 | 83 | 15.8 | 342 | 0.38 |

TABLE 2

| Water-absorbing agent | Not smaller than 850 μm % | 850-710 μm % | 710-600 μm % | 600-500 μm % | 500-425 μm % | 425-300 μm % | 300-212 μm % | 212-150 μm % | 150-45 μm % | Not larger than 45 μm % |
|---|---|---|---|---|---|---|---|---|---|---|
| D1-1A10 | 0.0 | 0.0 | 0.1 | 2.4 | 17.5 | 35.6 | 27.4 | 13.1 | 3.8 | 0.1 |
| D1-2A10 | 0.0 | 0.0 | 0.1 | 2.3 | 17.3 | 35.7 | 27.5 | 13.2 | 3.8 | 0.1 |
| D1-3A10 | 0.0 | 0.0 | 0.1 | 2.0 | 17.2 | 36.0 | 27.5 | 13.1 | 4.0 | 0.1 |
| D4-4A10 | 0.0 | 0.0 | 0.1 | 2.3 | 17.6 | 35.8 | 27.1 | 13.5 | 3.6 | 0.0 |
| D4-5A10 | 0.0 | 0.0 | 0.0 | 1.8 | 17.4 | 36.1 | 28.0 | 12.7 | 3.9 | 0.1 |
| D4-6A10 | 0.0 | 0.0 | 0.0 | 1.7 | 17.6 | 36.2 | 27.9 | 12.5 | 4.0 | 0.1 |
| D7-7A00 | 0.0 | 0.0 | 0.1 | 1.8 | 15.5 | 33.8 | 28.9 | 15.3 | 4.5 | 0.1 |
| D7-7A10 | 0.0 | 0.0 | 0.1 | 1.7 | 14.7 | 34.1 | 29.1 | 15.5 | 4.6 | 0.2 |
| D7-7A20 | 0.0 | 0.0 | 0.1 | 1.5 | 13.9 | 33.9 | 30.0 | 15.8 | 4.6 | 0.2 |
| D7-7A30 | 0.0 | 0.0 | 0.1 | 1.4 | 12.9 | 34.5 | 30.1 | 16.1 | 4.7 | 0.2 |
| D4-8A10 | 0.0 | 0.0 | 0.1 | 1.9 | 17.8 | 35.8 | 27.8 | 12.8 | 3.7 | 0.1 |
| D4-9A10 | 0.0 | 0.0 | 0.1 | 1.7 | 17.4 | 36.2 | 28.2 | 13.2 | 3.2 | 0.0 |
| D4-10A10 | 0.0 | 0.0 | 0.0 | 2.1 | 8.9 | 38.0 | 32.0 | 14.0 | 4.7 | 0.3 |
| D4-11A10 | 0.0 | 0.0 | 0.1 | 1.6 | 7.5 | 33.0 | 35.8 | 16.0 | 5.6 | 0.4 |
| D4-12A10 | 0.0 | 0.0 | 0.1 | 1.0 | 6.0 | 28.0 | 39.9 | 18.0 | 6.5 | 0.5 |
| D4-13A10D | 0.0 | 0.0 | 0.0 | 1.3 | 16.5 | 34.5 | 29.8 | 13.4 | 4.3 | 0.2 |
| D7-14A10D | 0.0 | 0.0 | 0.0 | 1.1 | 12.3 | 34.8 | 30.4 | 16.3 | 4.9 | 0.2 |
| D15-15A10 | 0 | 0 | 0 | 0.3 | 15.1 | 45.9 | 28 | 9.9 | 0.7 | 0.1 |
| D16-16A10 | 0.0 | 0.0 | 0.2 | 9.8 | 16 | 37.9 | 22.1 | 10.3 | 3.5 | 0.2 |
| D16-17A10 | 0.0 | 0.0 | 0.2 | 10.2 | 15.8 | 36.5 | 23.1 | 10.1 | 3.9 | 0.2 |

TABLE 3

| | Not smaller than 850 μm % | 850-710 μm % | 710-600 μm % | 600-500 μm % | 500-425 μm % | 425-300 μm % | 300-212 μm % | 212-150 μm % | 150-45 μm % | Not larger than 45 μm % |
|---|---|---|---|---|---|---|---|---|---|---|
| Water-absorbing agent | | | | | | | | | | |
| D16-18A10 | 0.0 | 0.0 | 0 | 9.5 | 14.9 | 38.6 | 22 | 11 | 3.8 | 0.2 |
| D15-19A10 | 0.0 | 0.0 | 0 | 0.3 | 15.1 | 45.9 | 28 | 9.9 | 0.7 | 0.1 |
| D15-20A10 | 0.0 | 0.0 | 0 | 0.1 | 15 | 44.2 | 28.1 | 11.3 | 1.1 | 0.2 |
| D15-21A10 | 0.0 | 0.0 | 0 | 0.3 | 15.4 | 47.8 | 27.6 | 8.2 | 0.6 | 0.1 |
| D4-22A10 | 0.0 | 0.0 | 0 | 1.7 | 17.3 | 36.2 | 27.9 | 12.8 | 4 | 0.1 |
| D23-23F10 | 0.0 | 0.0 | 0.1 | 2.5 | 17.3 | 35.4 | 27.4 | 13.3 | 3.9 | 0.1 |
| D16-24A10 | 0.0 | 0.0 | 0.1 | 12.1 | 17 | 36.4 | 21 | 10.1 | 3.2 | 0.1 |
| D15-25A10 | 0.0 | 0.0 | 0 | 0.2 | 15.1 | 45.1 | 28.2 | 10.2 | 1.1 | 0.1 |
| D16-26A10 | 0.0 | 0.0 | 0 | 10.1 | 16.2 | 38.2 | 21.3 | 11.1 | 2.9 | 0.2 |
| D4-27A10 | 0.0 | 0.0 | 0 | 5.9 | 24.1 | 39.1 | 19.6 | 9.1 | 2.1 | 0.1 |
| D15-28A10 | 0.0 | 0.0 | 0 | 0.2 | 17.1 | 49.2 | 24.1 | 8.6 | 0.7 | 0.1 |
| D16-29A10 | 0.0 | 0.0 | 0 | 11.3 | 16.4 | 36.3 | 22 | 10.2 | 3.6 | 0.2 |
| Comparative water-absorbing agent | | | | | | | | | | |
| Y1-1A00 | 0.1 | 3.5 | 25.2 | 15 | 12.5 | 23.3 | 11.2 | 5.2 | 3.8 | 0.2 |
| Y1-2A00 | 0.1 | 4.2 | 24.5 | 15.2 | 12.4 | 23.1 | 10.8 | 5.5 | 4 | 0.2 |
| Y1-3A00 | 0.0 | 2.9 | 24.3 | 14.9 | 11.9 | 24.3 | 11.4 | 6 | 4.1 | 0.2 |
| Y1-4A00 | 0.0 | 2.8 | 24.1 | 14.8 | 11.8 | 24.3 | 10.8 | 6.9 | 4.3 | 0.2 |
| Y5-5A00 | 0.0 | 3.1 | 24.4 | 15.1 | 11.6 | 24.2 | 10.9 | 6.8 | 3.7 | 0.2 |
| Y6-6A00 | 0.0 | 0.0 | 0.3 | 10.3 | 17.7 | 35.4 | 22.1 | 9.7 | 4.3 | 0.2 |

(As to Water-Absorbing Agents as Obtained from Examples 1 to 23 and Comparative Examples 1 to 6):

All the water-absorbing agents as obtained from Examples 1 to 23 of the present invention satisfy the relational expression "SFC≧260−8·CSF" of the present invention and are excellent in both of the liquid permeability and the capillary suction force. On the other hand, as to the comparative water-absorbing agents as obtained from Comparative Examples 1 to 6, the mass-average particle diameter or the logarithmic standard deviation of the particle diameter distribution is improper, or the water-extractable component content is high. Therefore, although some of the comparative water-absorbing agents are excellent in the liquid permeability or the capillary suction force, the comparative water-absorbing agents are not excellent in both them.

Figure 6:
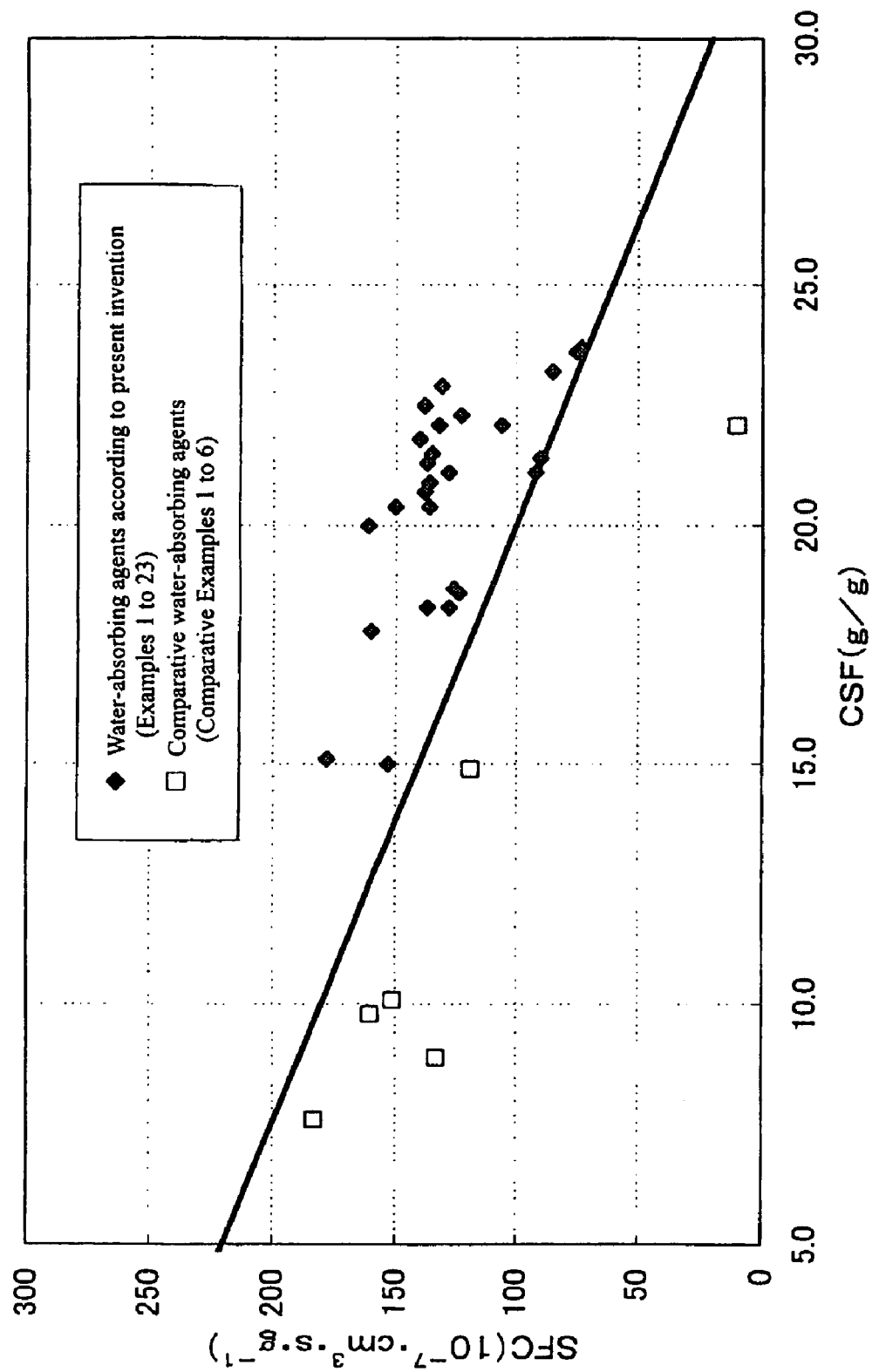
FIG. 6 is a graph of which: the horizontal axis shows the CSF (g/g), and the vertical axis shows the SFC ($10^{-7} \cdot cm^3 \cdot s \cdot g^{-1}$). This graph shows that the water-absorbing agents as obtained from the Examples of the present invention have higher liquid permeability and capillary suction force than the comparative water-absorbing agents as obtained from the Comparative Examples.

The CSF-SFC plots of the water-absorbing agents 1 to 23 according to the present invention and of the comparative water-absorbing agents 1 to 6 are shown in FIG. 6.

Figure 7:
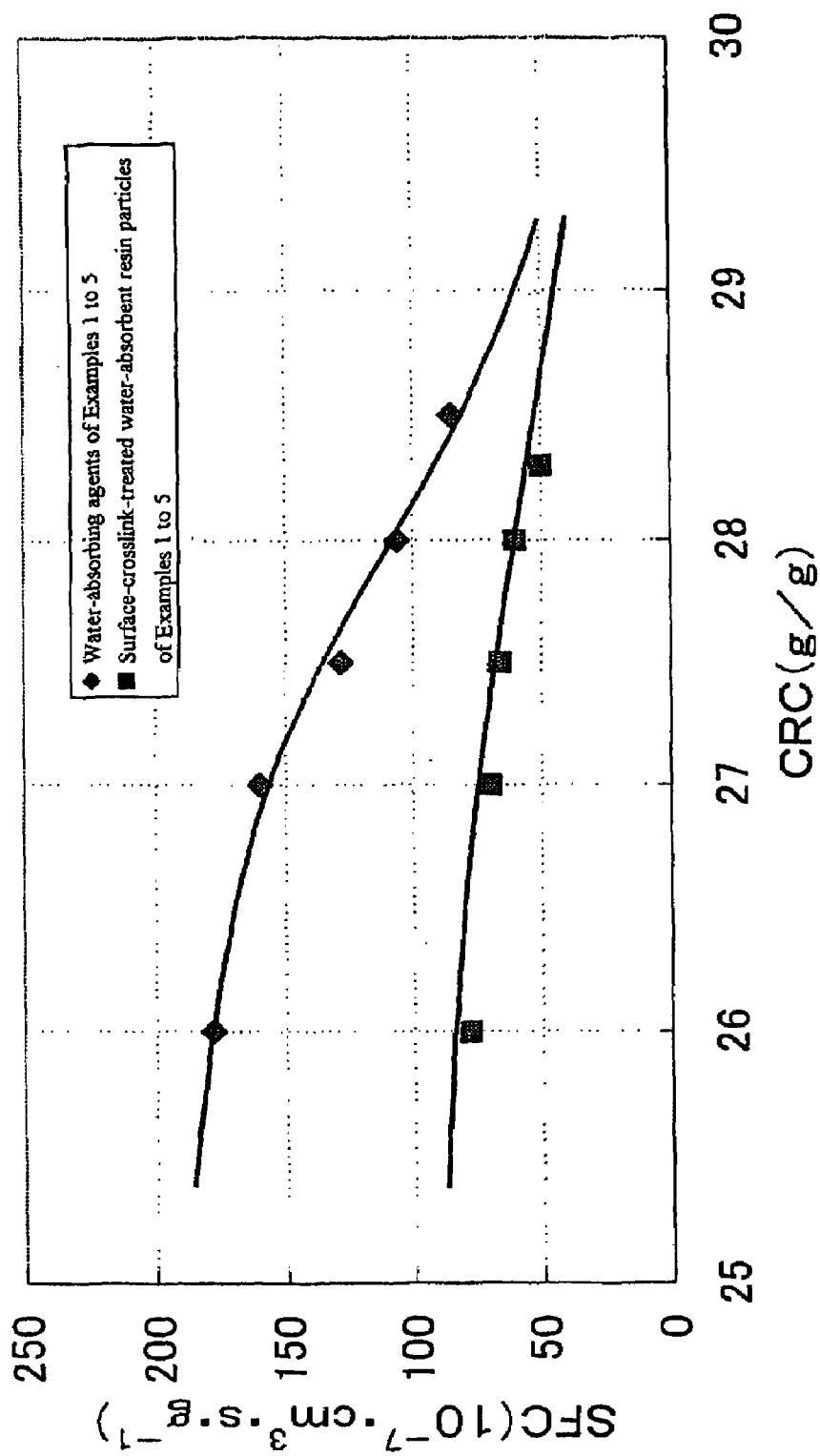
FIG. 7 is a graph of which: the horizontal axis shows the CRC (g/g), and the vertical axis shows the SFC ($10^{-7} \cdot cm^3 \cdot s \cdot g^{-1}$). Plotted thereon are the CRC and SFC of the surface-crosslink-treated water-absorbent resin particles and of the water-absorbing agents according to the present invention, wherein the surface-crosslink-treated water-absorbent resin particles and the water-absorbing agents according to the present invention are those which are described in Examples 1 to 5. It is shown that the effects of the liquid-permeability-enhancing agent (β) are remarkably high when the CRC is less than 29 g/g.

(As to Water-Absorbing Agents as Obtained from Examples 1 to 5):

Examples 1 to 5 show that the effects of the liquid-permeability-enhancing agent (β) vary with the variation of the CRC. The plots of the CRC and SFC before the addition of the liquid-permeability-enhancing agent (β) (those of the surface-crosslink-treated water-absorbent resin particles) and those after the addition of the liquid-permeability-enhancing agent (β) (those of the water-absorbing agents according to the present invention) are shown in FIG. 7. From this FIG. 7, the effects of the liquid-permeability-enhancing agent (β) can be considered as excellent particularly when the CRC is less than 29 g/g.

(As to Water-Absorbing Agent as Obtained from Example 7):

From the comparison between the water-absorbing agents as obtained from this Example, it can be understood that, as the ratio of the agglomerated water-absorbent resin particles as contained in the water-absorbent resin particles increases, the capillary suction force (CSF) of the resultant water-absorbing agent becomes larger. Therefore, the water-absorbing agent according to the present invention favorably, comprises the liquid-permeability-enhancing agent (β) and the surface-treated water-absorbent resin particles containing the agglomerated water-absorbent resin particles. That is to say, it is favorable that at least a portion of the water-absorbent resin particles included in the water-absorbing agent have a porous structure.

(As to Water-Absorbing Agents as Obtained from Examples 13 and 14):

Even after mechanical damage has been done to the water-absorbing agents according to the present invention, these water-absorbing agents display excellent performances. Therefore, these water-absorbing agents are advantageous also in the case of being commercially produced.

INDUSTRIAL APPLICATION

The water-absorbing agent as obtained in the present invention can be used particularly favorably for sanitary materials for absorption of excrement, urine, or blood, such as disposable diapers and sanitary napkins.

The invention claimed is:

1. A water-absorbing agent, which is a particulate water-absorbing agent comprising water-absorbent resin particles (α) and a liquid-permeability-enhancing agent (β), wherein said water-absorbent resin particles (α) are prepared by crosslinking with a surface-crosslinking agent the surface of irregular-shaped pulverized particles of a crosslinked polymer made from a monomer comprising acrylic acid and/or its salt;

wherein the particulate water-absorbing agent has:
a mass-average particle diameter in the range of 234 to 394 µm, a logarithmic standard deviation ($\sigma\zeta$) of a particle diameter distribution in the range of 0.25 to 0.45, an absorption capacity of not less than 15 g/g without load, and a water-extractable component content of not higher than 15 mass %; and further
a liquid-permeability-enhancing agent ($\beta$) content in the range of 0.01 to 5 mass parts per 100 mass parts of the water-absorbent resin particles ($\alpha$).

2. A water-absorbing agent according to claim 1, wherein the water-absorbent resin particles ($\alpha$) included in the water-absorbing agent include particles having a porous structure.

3. A water-absorbing agent according to claim 1 or 2, which includes particles having particle diameters in the range of 100 to 500 µm in an amount of not smaller than 80 mass % relative to the water-absorbing agent.

4. A water-absorbing agent according to claim 1 or 2, wherein the water-absorbing agent has a mass ratio (particles having particle diameters of not smaller than 300 µm)/(particles having particle diameters of smaller than 300 µm) in the range of 80/20 to 20/80.

5. A water-absorbing agent according to claim 1 or 2, wherein the water-absorbing agent displays a capillary absorption capacity of not less than 15 g/g for a 0.90 mass % physiological saline solution.

6. A water-absorbing agent according to claim 1 or 2, wherein the water-absorbing agent displays a saline flow conductivity of not less than 50 ($10^{-7} \cdot cm^3 \cdot s \cdot g^{-1}$) for a 0.69 mass % physiological saline solution.

7. A water-absorbing agent according to claim 1 or 2, wherein the absorption capacity of the water-absorbing agent without load is less than 29 g/g.

8. A water-absorbing agent according to claim 1 or 2, wherein the liquid-permeability-enhancing agent ($\beta$) includes water-insoluble hydrophilic inorganic fine particles and/or a water-soluble polyvalent metal salt.

9. A water-absorbing agent according to claim 1, wherein the water-absorbing agent is obtained by forming the surface-crosslinked water-absorbent resin particles and thereafter mixing the surface-crosslinked water-absorbent resin particles with the liquid-permeability-enhancing agent.

10. A water-absorbing agent according to claim 9, wherein the liquid-permeability-enhancing agent is added as an aqueous solution, slurry or powder.

11. A water-absorbing agent according to claim 1, wherein the liquid-permeability-enhancing agent is mixed with the surface-crosslinked water-absorbent resin particles in an amount sufficient to increase the saline flow conductivity of the water-absorbent agent.

12. A water-absorbing agent according to claim 11, wherein the liquid-permeability-enhancing agent is added as a powder to the surface-crosslinked water-absorbent resin particles.

\* \* \* \* \*